US010281451B2

(12) United States Patent
Mycek et al.

(10) Patent No.: US 10,281,451 B2
(45) Date of Patent: May 7, 2019

(54) METHOD OF DETERMINING THE VIABILITY OF AT LEAST ONE CELL

(71) Applicant: The Regents of the University of Michigan, Ann Arbor, MI (US)

(72) Inventors: Mary-Ann Mycek, Ann Arbor, MI (US); Stephen Feinberg, Ann Arbor, MI (US); Cynthia Marcelo, Ann Arbor, MI (US); William Lloyd, Wixom, MI (US); Leng-Chun Chen, Ann Arbor, MI (US); Shiuhyang Kuo, Dexter, MI (US); Hyungjin Myra Kim, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/323,790

(22) Filed: Jul. 3, 2014

(65) Prior Publication Data
US 2014/0363840 A1    Dec. 11, 2014

Related U.S. Application Data

(63) Continuation-in-part of application No. PCT/US2013/021268, filed on Jan. 11, 2013.
(Continued)

(51) Int. Cl.
*G01N 33/483* (2006.01)
*G01N 21/64* (2006.01)
(Continued)

(52) U.S. Cl.
CPC ..... *G01N 33/4833* (2013.01); *G01N 21/6408* (2013.01); *G01N 21/6456* (2013.01);
(Continued)

(58) Field of Classification Search
CPC .......... G01N 33/4833; G01N 21/6408; G01N 21/6456; G01N 33/5005; G01N 33/5735;
(Continued)

(56) References Cited

U.S. PATENT DOCUMENTS 7,887,829 B1    2/2011 Feinberg et al.

FOREIGN PATENT DOCUMENTS

WO    WO 2010/030964    *  3/2010    ............. A61L 27/54

OTHER PUBLICATIONS

Niesner et al., Noniterative Biexponential Fluorescence Lifetime Imaging in the Investigation of Cellular Metabolism by Means of NAD(P)H Autofluorescence, ChemPhysChem, 2004, 5, pp. 1141-1149.*
(Continued)

*Primary Examiner* — Jennifer M. H. Tichy
(74) *Attorney, Agent, or Firm* — Howard & Howard Attorneys PLLC

(57) ABSTRACT

This disclosure provides a method of determining the viability of at least one cell via quantification of nicotinamide adenine dinucleotide (phosphate) (NAD(P)H), flavin adenine dinucleotide (FAD), and/or collagen. The method includes the steps of contacting the at least one cell with light having a wavelength of from 700 to 900 nm, using two photon excitation, or from 335 to 400 nm, using one photon excitation, to induce an optical response from the NAD(P)H, FAD, and/or collagen and measuring the optical response. The method also includes the step of quantifying one or more of an amount, spatial localization, and/or time-dependent response of the NAD(P)H, FAD, and/or collagen utilizing the optical response.

24 Claims, 17 Drawing Sheets

Related U.S. Application Data

(60) Provisional application No. 61/585,827, filed on Jan. 12, 2012.

(51) Int. Cl.
  *G01N 33/50* (2006.01)
  *G01N 33/58* (2006.01)
  *G01N 33/68* (2006.01)
  *G01N 33/573* (2006.01)

(52) U.S. Cl.
  CPC ..... *G01N 33/5005* (2013.01); *G01N 33/5735* (2013.01); *G01N 33/582* (2013.01); *G01N 33/6887* (2013.01); *G01N 2333/46* (2013.01); *G01N 2333/78* (2013.01)

(58) Field of Classification Search
  CPC ............. G01N 33/582; G01N 33/6887; G01N 2333/46; G01N 2333/78
  USPC .......................................................... 435/29
  See application file for complete search history.

(56) References Cited

OTHER PUBLICATIONS

MacNeil, Progress and opportunities for tissue-engineered skin, Nature, vol. 445, Feb. 22, 2007, pp. 874-880.*
Chen et al., Nonlinear optical molecular imaging enables metabolic redox sensing in tissue-engineered constructs, Proceedings of SPIE 8089, Molecular Imaging III, 80890J1-7 (Jun. 15, 2011).*
Chandra et al., Sensing metabolic activity in tissue engineered constructs, Diagnostic Optical Spectroscopy in Biomedicine IV, Proceedings of SPIE-OSA Biomedical Optics, SPIE vol. 6628, 66280B1-6 (2007).*
Skala et al., In vivo multiphoton microscopy of NADH and FAD redox states, fluorescence lifetimes, and cellular morphology in precancerous epithelia, PNAS, vol. 104, No. 49 (Dec. 4, 2007) pp. 19494-19499.*
Ramanujam, Autofluorescence spectroscopy of normal and malignant human breast cell lines, Photochemistry and Photobiology, 2003, vol. 78, No. 5, pp. 462-469.
Rice, Two-photon microscopy for non-invasive, quantitative monitoring of stem cell differentiation. PloS ONE (www.plosone.org), Apr. 2010, vol. 5, Issue 4, e10075, whole document.
Wong, Two-photon excitation laser scanning microscopy of human, porcine, and rabbit nasal septal cartilage, Tissue Engineering, 2001, vol. 7, No. 5, pp. 599-606.
Yu, Two-photon autofluorescence dynamics imaging reveals sensitivity of intracellular NADH concentration and conformation to cell physiology at the single-cell level, J Photochem Photobiol B., 2009, vol. 95, No. 1, pp. 46-57.
Xu, Two-photon fluorescence spectroscopy for identification of healthy and malignant biological tissues, Proceedings of SPIE, 2000, vol. 3921, pp. 249-254.
International Search Report dated Apr. 24, 2013, for International Application PCT/US2013/021268.

* cited by examiner

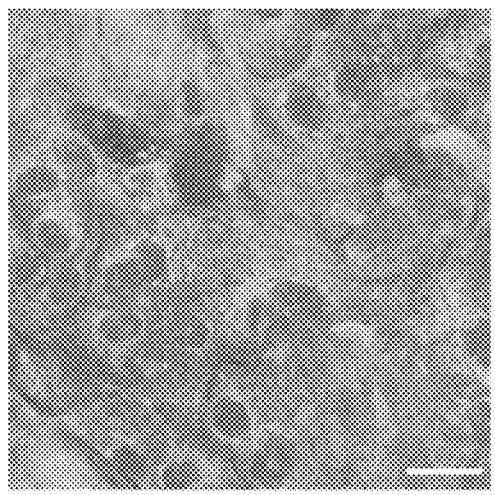
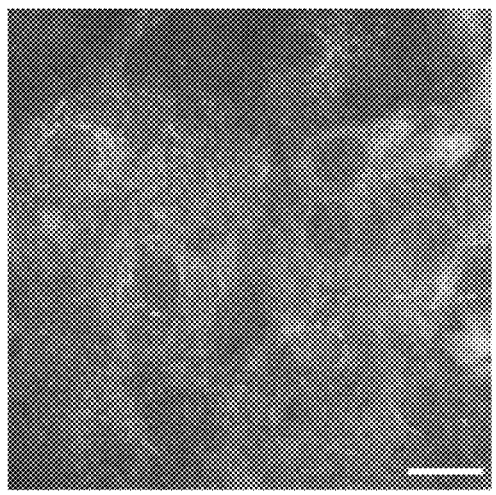
FIG. 1A　　　　　　　FIG. 1B
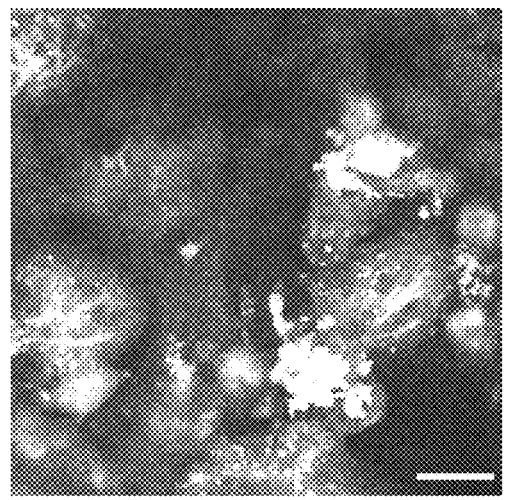
FIG. 2A　　　　　　　FIG. 2B

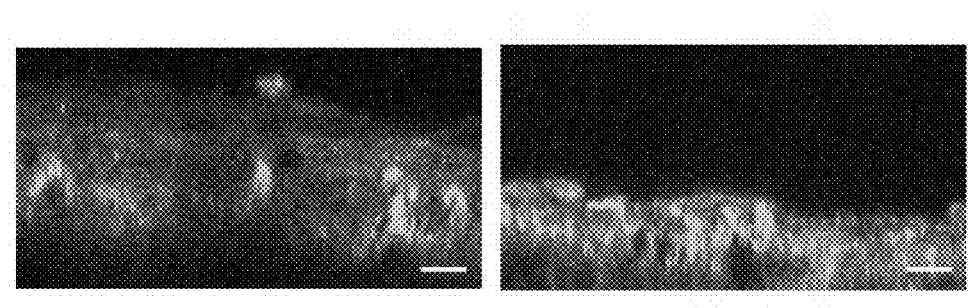
*FIG. 5A*  *FIG. 5B*
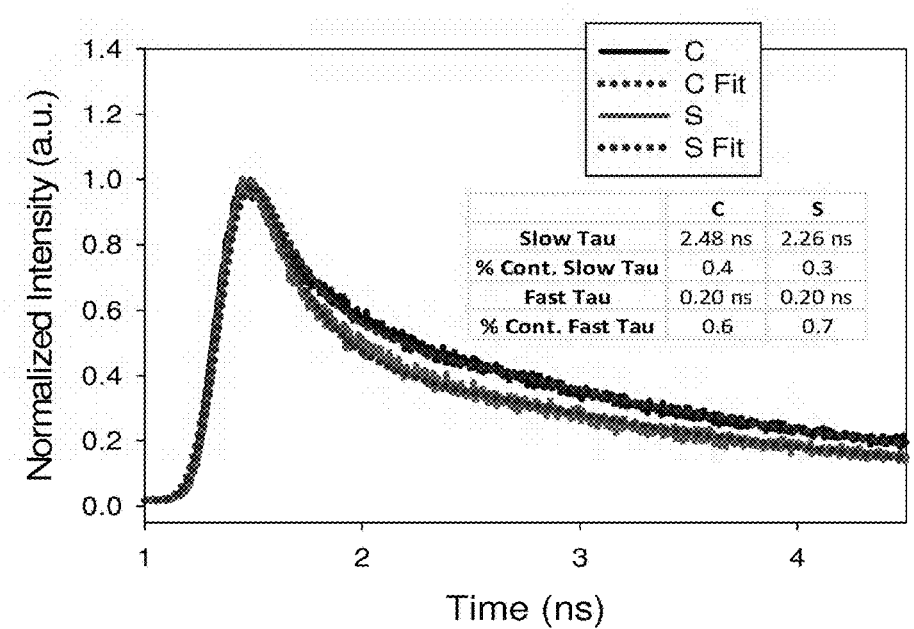
*FIG. 6*

METHOD OF DETERMINING THE VIABILITY OF AT LEAST ONE CELL

CROSS-REFERENCE TO RELATED APPLICATION

This application is a Continuation-In-Part of International Application No. PCT/US2013/021268, filed on Jan. 11, 2013, which claims priority to U.S. Ser. No. 61585827, filed on Jan. 1, 2012, wherein the disclosures of each are expressly incorporated herein by reference in various non-limiting embodiments.

GOVERNMENT LICENSE RIGHTS

This invention was made with government support under DE019431 awarded by the National Institutes of Health. The government has certain rights in the invention.

This disclosure relates to a method of determining the viability of at least one cell. More specifically, this disclosure relates to quantifying nicotinamide adenine dinucleotide (phosphate) (NAD(P)H), flavin adenine dinucleotide (FAD), and/or collagen.

The fields of tissue-engineering and regenerative medicine have evolved such that tissue burns, removed tumors, or open wounds can be replaced with tissue developed from patients' primary cells. However, quality control mandated evaluations are required and typically must be completed in real time, e.g. during manufacturing within the first hours after construct maturation and prior to implantation. Currently, a limited number of techniques, each with significant drawbacks, are utilized. For example, analysis of histology sections of the tissues and biochemical analysis of spent culture mediums for indicator substances can be employed. Histology accurately preserves a cross sectional slice of the tissue, but is limited because the technique is destructive, time consuming, not cost effective, and limited to only a portion of the tissue. Biochemical analysis of spent culture mediums identifies glucose consumption and protein production by viable cells but is not reliable. Perhaps most importantly, neither technique can be used to locally measure cellular metabolic function from growing cells in real time. A satisfactory evaluation method to assess tissue for local viability, serving as an estimation of growth potential during culturing and as a release criterion prior to implantation, is desirable.

SUMMARY OF THE DISCLOSURE

The instant disclosure provides a method of determining the viability of at least one cell via quantification of nicotinamide adenine dinucleotide (phosphate) (NAD(P)H), flavin adenine dinucleotide (FAD), and/or collagen. The method includes the steps of contacting the at least one cell with light having a wavelength of from 700 to 900 nm, using two photon excitation, or from 335 to 400 nm, using one photon excitation, to induce an optical response from the NAD(P)H, FAD, and/or collagen and measuring the optical response. The method also includes the step of quantifying one or more of an amount, spatial localization, and/or time-dependent response of the NAD(P)H, FAD, and/or collagen utilizing the optical response.

BRIEF DESCRIPTION OF THE FIGURES

Other advantages and aspects of the disclosure are described in the following detailed description and accompanying figures wherein:

FIGS. 1A and 1B are representative NAD(P)H fluorescence images of control (1A) and starved EVPOMEs (1B) of the Examples wherein the scale bar is 25 μm;

FIGS. 2A and 2B are representative FAD fluorescence images of control (2A) and 3.6 mM stressed EVPOMEs (2B) of the Examples wherein the scale bar is 25 μm;

FIGS. 5A and 5B are representative NAD(P)H cross-sectional images of control (5A) and Rapamycin cultured EVPOMEs (5B) of the Examples wherein the scale bar is 50 μm;

FIG. 6 is a representative line graph illustrating average NAD(P)H fluorescence decays with fits of (C) control and (S) thermally-stressed dish keratinocytes of the Examples;

DETAILED DESCRIPTION OF THE DISCLOSURE

Figure 3A:
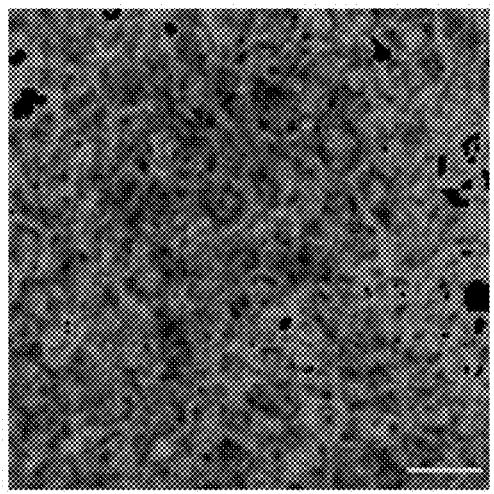
FIGS. 3A and 3B are representative redox ratio maps of control (3A) and thermally-stressed EVPOMEs (3B) of the Examples wherein the scale bar is 25 μm.

The instant disclosure provides a method of determining the viability of at least one cell. Alternatively, the method may be described as a method of determining whether the at least one cell is alive, whether the at least one cell is respirating, and/or whether one or more mitochondria of the at least one cell are producing respiration intermediates. Typically, the method is utilized to determine whether the at least one cell can be utilized in surgery, for transplant, in grafts, etc. As is known in the art, cells typically must be viable if they are to be successfully incorporated into a living body. Alternatively, the method may be utilized to determine the location of living and dead (i.e., viable and not-viable) cells and may, for example, be utilized to determine proper locations for amputations, biopsies, etc.

The at least one cell may be alternatively described as a monolayer of one or more cells or as two or more layers of one or more cells. Alternatively, the at least one cell may be further defined as one or more layers of tissue. The tissue may be human or non-human, e.g. animal, mammalian, etc. The at least one cell may be alternatively described as a plurality of cells or as a tissue construct or a tissue culture. In another embodiment, the at least one cell is a human cell, such as a skin cell, internal organ cell, optical or aural cell, gland cell, keratinizing epithelial cell, cell from internal organs, mucosal membrane cell, oral cell, brain cell, stem cell, hepatocytes, myocyte, keratinocyte, etc. Alternatively, the at least one cell may be described as an Ex Vivo Produced Oral Mucosa Equivalent (EVPOME). In various embodiments, the one of more cells, e.g. EVPOMEs, are formed or present in a mono-, bi-, three-, or multilayered structure. For example, the at least one cell may be formed into a three-layered structure including, for example, a top keratin layer, a middle living cell layer, and a bottom dermal equivalent layer. In one embodiment, it is contemplated that metabolic activity of an EVPOME is contained solely, or almost entirely, within the middle living cell layer of a tissue construct. In another embodiment, the at least one cell is further defined as a tissue-engineered EVPOME construct, e.g. a 3-dimensional tissue with a surface layer of keratin (about 10-20 µm thick), a subsurface layer of keratinocytes (about 40 µm thick), and a base that includes collagen (about 400-500 µm thick). It is contemplated that the method may be utilized with any cell, tissue, organ, etc. Any of the cells or tissues described below may be alternatively described, in one or more non-limiting embodiments, as any one or more of the cells/tissues described above.

The viability of the at least one cell is determined via quantification of nicotinamide adenine dinucleotide (phosphate) (NAD(P)H), flavin adenine dinucleotide (FAD), and/or collagen. In one embodiment, the viability is determined via quantification of NAD(P)H. In another embodiment, the viability is determined via quantification of FAD. In still another embodiment, the viability is determined via quantification of collagen. In still other embodiments, the viability is determined via quantification of NAD(P)H and FAD, or NAD(P)H and collagen, or FAD and collagen, and/or any combination thereof. It is also contemplated that quantification of keratin may also be utilized in conjunction with any of the above or on its own in this method. The method may also include quantification and/or qualitative evaluation of one or more additional biological compounds, e.g. cellular metabolic compounds, in addition to the quantification of NAD(P)H, FAD, and/or collagen and/or keratin.

The terminology "quantification" may describe the quantitative evaluation of one or more the aforementioned compounds. Alternatively, the terminology may describe the counting or numerical determination of amounts (e.g., mass/weight, molar amount, weight percent, volume percent, etc.) and/or location (e.g. spatial location), and/or response (e.g. time-dependent response) of one or more of the aforementioned compounds, as further described below. The quantification may be alternatively described as applying a mathematical formula, algorithm, etc. to a series of data and/or numerical observations.

Metabolic function of the one or more cells can be noninvasively measured because cellular metabolic molecules, including autofluorescence from NAD(P)H and FAD, can intrinsically fluoresce without adding exogenous chemicals. NAD(P)H and FAD are both coenzymes present in the oxidative phosphorylation cycle, whose concentrations are directly related to the glucose uptake by the cells. An accurate gauge of metabolic activity can be reported from NAD(P)H and FAD because these molecules are typically fluorescent in their reduced and oxidized forms, respectively. In addition, (NAD(P)H), a coenzyme largely produced by actively metabolizing cells to synthesize membrane lipids can be used to determine cellular viability. Actively metabolizing cells typically have a unique concentration of NAD(P)H and FAD as compared to non-functioning cells, directly relating to their fluorescence intensity. Accordingly, the quantification or NAD(P)H, FAD, and/or collagen can be utilized to determine cellular viability.

NAD/NAD(P)H

Nicotinamide adenine dinucleotide, abbreviated $NAD^+$, is a coenzyme found in all living cells. The compound is a dinucleotide, because it includes two nucleotides joined through their phosphate groups. One nucleotide includes an adenine base and the other includes nicotinamide. In metabolism, $NAD^+$ is involved in redox reactions, carrying electrons from one reaction to another. The coenzyme is, therefore, found in two forms in cells. $NAD^+$ is an oxidizing agent and accepts electrons from other molecules and becomes reduced. This reaction forms NADH, which can then be used as a reducing agent to donate electrons. These electron transfer reactions are the main function of $NAD^+$.

Both $NAD^+$ and NADH absorb ultraviolet light because of their adenine moiety. For example, peak absorption of $NAD^+$ is typically at a wavelength of 259 nanometers (nm), with an extinction coefficient of about 16,900 $M^{-1}$ $cm^{-1}$. NADH also typically absorbs at higher wavelengths, with a second peak in UV absorption at about 339 nm with an extinction coefficient of about 6,220 $M^{-1}$ $cm^{-1}$.

$NAD^+$ and NADH also typically differ in their fluorescence. NADH in solution typically has an emission peak at about 460 nm and a fluorescence lifetime of about 0.4 nanoseconds (free NADH), while the oxidized form of the coenzyme typically does not fluoresce. The properties of the fluorescence signal changes when NADH binds to proteins, so these changes can be used to measure dissociation constants. These changes in fluorescence can also used to measure changes in the redox state of living cells.

$NAD^+$ may be converted into nicotinamide adenine dinucleotide phosphate ($NADP^+$) which is a coenzyme used in anabolic reactions, such as lipid and nucleic acid synthesis, and which requires NAD(P)H as a reducing agent. NAD(P)H is the reduced form of $NADP^+$. $NADP^+$ differs from $NAD^+$ in the presence of an additional phosphate group on the 2' position of the ribose ring that carries the adenine moiety. However there are other mechanisms of generating NAD(P)H, many of which depend on the presence of mitochondria. The enzymes in these processes tend to be NADP-linked malic enzyme, NADP-linked isocitrate dehydrogenase, and nicotinamide nucleotide transhydrogenase. The isocitrate dehydrogenase mechanism appears to be the major source of NAD(P)H in fat and possibly also liver cells. Also in mitochondria, NADH kinase produces NAD(P)H and ADP using NADH and ATP as substrates.

NAD(P)H provides reducing equivalents for biosynthetic reactions and oxidation-reduction involved in protecting against the toxicity of reactive oxygen species, allowing the regeneration of GSH (reduced glutathione). NAD(P)H is also used in anabolic pathways, such as lipid synthesis, cholesterol synthesis, and fatty acid chain elongation. NAD(P)H may also play a role in generating free radicals in immune cells.

FAD

Flavin adenine dinucleotide (FAD) is a redox cofactor involved in several reactions in cellular metabolism. FAD can typically exist in two different redox states. FAD includes a riboflavin moiety bound to a phosphate group of an ADP molecule. FAD can be reduced to $FADH_2$ after accepting two hydrogen atoms. More specifically, FAD, in a fully oxidized form, accepts two electrons and two protons to become $FADH_2$. $FADH_2$ can then be oxidized to a semi-reduced form FADH by donating one electron and one proton. The FADH can then be oxidized once more by losing an electron and a proton to return to FAD.

The primary biochemical role of $FADH_2$ is typically to carry high-energy electrons used for oxidative phosphorylation. FAD is a prosthetic group in the enzyme complex succinate dehydrogenase that oxidizes succinate to fumarate in the eighth step of the citric acid cycle. The high-energy electrons from this oxidation are stored momentarily by reducing FAD to $FADH_2$. $FADH_2$ then reverts to FAD, sending its two high-energy electrons through the electron transport chain. Another metabolic source of $FADH_2$ is beta oxidation, where FAD serves as a coenzyme to acyl CoA dehydrogenase.

Collagen

Collagen is a group of proteins and is composed of a triple helix, which generally includes of two identical chains ($\alpha 1$) and an additional chain that differs slightly in its chemical composition ($\alpha 2$). The amino acid composition of collagen is atypical for proteins, particularly with respect to a high hydroxyproline content. The most common motifs in the amino acid sequence of collagen are glycine-proline-X and glycine-X-hydroxyproline, wherein X is any amino acid other than glycine, proline or hydroxyproline.

Collagen is typically formed both inside and outside of cells. For example, inside cells, two types of peptide chains are typically formed during translation on ribosomes along the rough endoplasmic reticulum (RER): alpha-1 and alpha-2 chains. These peptide chains have registration peptides on each end and a signal peptide. Subsequently, polypeptide chains are released into the lumen of the RER and signal peptides are cleaved inside the RER. Then, hydroxylation of lysine and proline amino acids occurs utilizing vitamin C as a co-factor. Then, glycosylation of specific hydroxylysine residues occurs followed by formation of a triple $\gamma$ helical structure inside the ER. Collagen may then be secreted by exocytosis. Outside of cells, for example, registration peptides may be cleaved and tropocollagen may be formed by procollagen peptidase. Multiple tropocollagen molecules may then form collagen fibrils, via covalent cross-linking, which links hydroxylysine and lysine residues. Multiple collagen fibrils may then form into collagen fibers. Collagen may be attached to cell membranes via several types of protein, including fibronectin and integrin.

As described in greater detail below, the quantification of one or more of NAD(P)H, FAD, and/or collagen can be used to determine the viability of the at least one cell. Said differently, the amounts, spatial location, and/or time-dependent response of the NAD(P)H, FAD, and/or collagen can be used to determine whether a cell or tissue is alive, as described in greater detail below.

Contacting the at Least One Cell with Light

Referring back to the method, the method includes the step of contacting (e.g. exciting) the at least one cell with light having a wavelength of from 700 to 900 nm (e.g. using two photon excitation) or 335 to 400 nm (e.g. using one photon excitation) to induce an optical response from the NAD(P)H, FAD, and/or collagen. In various embodiments, the wavelength may be further defined as from 705 to 895, from 710 to 890, from 715 to 885, from 720 to 880, from 725 to 875, from 730 to 870, from 735 to 865, from 740 to 860, from 745 to 855, from 750 to 850, from 755 to 845, from 760 to 840, from 765 to 835, from 770 to 830, from 775 to 825, from 780 to 820, from 785 to 815, from 785 to 810, from 790 to 805, from 795 to 800, or from 330 to 395, from 335 to 390, from 340 to 385, from 345 to 380, from 350 to 375, from 355 to 370, and from 360 to 365, nm. For example, in embodiments wherein an optical response is desired from NAD(P)H, the wavelength is typically, but is not limited to, from 685 to 720, from 690 to 715, from 695 to 710, from 700 to 705, from 695 to 705, about 700, or about 705, nm. In other embodiments, wherein an optical response is desired from FAD, the wavelength is typically, but is not limited to, from 885 to 915, from 890 to 910, from 895 to 905, from 895 to 900, from 900 to 905, or about 900, nm. It is contemplated that wavelength may be alternatively described as any value, or range of values, both whole and fractional, within or between any one or more values described above. In various embodiments, the aforementioned mesh size may vary by ±1, 2, 3, 4, 5, 6, 7, 8, 9, 10, 15, 20, 25, 30, etc. %.

The light may be generated using any light source, for example, using a laser, lamp, light emitting diode, etc. For example, a Leica TCS SP5 microscope equipped with a Ti:sapphire laser (Mai Tai, Spectral-Physics), or similar, may be used. An excitation laser source and emission light can be coupled through an inverted microscope with 40× (1.25 NA)/63× (1.4 NA) oil immersion objective lenses and a 25× water immersion objective lens (0.95 NA, 2.5 mm working distance). In other embodiments, the light is generated using one or more of a 2-photon tunable laser, a 1-photon laser, a super continuum white light laser, a high-repetition rate microchip laser, a steady-state laser diode, a gas laser, e.g. including argon, helium, neon, nitrogen, krypton, or xenon ions, a dye laser with a UV/Vis dye, a chemical laser, and/or a metal-vapor laser.

Optical Response

The optical response may be further defined as any emission, reflection, or refraction of light from one or more of the NAD(P)H, FAD, and/or collagen, at the same or different wavelengths as the excitation light, i.e., the light that is used in the method to contact the at least one cell, as described immediately above. For example, the optical response may be further defined as fluorescence, phosphorescence, luminescence, bioluminescence, chemiluminescence, etc. In one embodiment, the optical response is further defined as fluorescence.

Fluorescence typically occurs when an orbital electron of a molecule, atom or nanostructure relaxes to its ground state by emitting a photon of light after being excited to a higher quantum state by some type of energy according to the formulas:

$S_0 + h\nu_{excitation} \rightarrow S_1$      Excitation:

$S_1 \rightarrow S_0 + h\nu_{emission} + \text{heat}$      Fluorescence (Emission):

wherein hv is photon energy, h is Planck's constant, v is frequency of light, $S_0$ is the ground state of the fluorophore (fluorescent molecule), and $S_1$ is the first (electronically) excited state.

A molecule in $S_1$ can relax by various competing pathways. For example, the molecule can undergo "non-radiative relaxation" in which the excitation energy is dissipated as heat (vibrations). Excited molecules can also relax via conversion to a triplet state, which may subsequently relax via phosphorescence or by a secondary non-radiative relaxation step. Relaxation of an $S_1$ state can also occur through interaction with a second molecule through fluorescence quenching, e.g. with molecular oxygen.

The efficiency of fluorescence is typically reported as a quantum yield, i.e., the ratio of the number of photons emitted to the number of photons absorbed:

Φ=Number of Photos Emitted/Number of Photons Absorbed

However, quantum yield can also be reported as the rate of excited state decay:

$\Phi = k_f / \Sigma_i k_i$ where $k_f$ is the rate of spontaneous emission of radiation and $\Sigma_i k_i$ is the sum of all rates of excited state decay. Other rates of excited state decay are caused by mechanisms other than photon emission and are, therefore, often called "non-radiative rates", which can include: dynamic collisional quenching, near-field dipole-dipole interaction (or resonance energy transfer), internal conversion, and intersystem crossing.

Fluorescence can also be reported relative to lifetime, i.e., an average time a molecule stays in its excited state before emitting a photon. Fluorescence typically follows first-order kinetics:

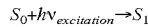

wherein $S_1$ is the concentration of excited state molecules at time t, $[S_1]_0$ is the initial concentration and Γ is the decay rate or the inverse of the fluorescence lifetime. Various radiative and non-radiative processes can de-populate the excited state. In such case the total decay rate is the sum over all rates:

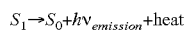

Alternatively, the optical response may be further defined as Second Harmonic Generation (SHG) or frequency doubling. SHG is a nonlinear optical process, in which photons interacting with a nonlinear material are combined to form new photons with twice the energy, and therefore twice the frequency and half the wavelength of the initial photons. SHG can be categorized in one of three classes, denoted 0, I and II. In Type 0 SHG, two photons having extraordinary polarization with respect to a crystal will combine to form a single photon with double the frequency/energy and extraordinary polarization. In Type I SHG, two photons having ordinary polarization with respect to a crystal will combine to form one photon with double the frequency and extraordinary polarization. In Type II SHG, two photons having orthogonal polarizations will combine to form one photon with double the frequency and extraordinary polarization. In this disclosure, SHG can be utilized for optical microscopy. Because of a non-zero second harmonic coefficient, only non-centrosymmetric structures are typically capable of emitting SHG light. One such structure is collagen, as described above.

In various embodiments, the optical response is further defined as fluorescence, e.g. emission at a wavelength of from 400 to 500, from 405 to 495, from 410 to 490, from 415 to 485, from 420 to 480, from 425 to 475, from 430 to 470, from 435 to 465, from 440 to 460, from 455 to 450, from 500 to 600, from 505 to 595, from 510 to 590, from 515 to 585, from 520 to 580, from 525 to 575, from 530 to 570, from 535 to 565, from 540 to 560, from 545 to 555, or from 550 to 555, nm. In other embodiments, the optical response is further defined as second harmonic generation which itself may be further defined as emission at a wavelength that is half the 2-photon excitation wavelength ±5 nm. It is contemplated that wavelength may be alternatively described as any value, or range of values, both whole and fractional, within or between any one or more values described above. In various embodiments, the aforementioned mesh size may vary by ±1, 2, 3, 4, 5, 6, 7, 8, 9, 10, 15, 20, 25, 30, etc. %.

Measuring the Optical Response

The method also includes the step of measuring the optical response. The optical response can be measured, for example, using non-linear optical microscopy. The optical response may be measured using filter fluorometers, spectrofluorometers, fluorometers or fluorimeters. Alternatively, the optical response may be measured using photomultiplier tubes, avalanche photodiodes, or streak cameras with wavelength selective optics. These wavelength selective optics include, but are not limited to, spectrometers, band pass filters, high pass filters, low pass filters, acousto-optic tunable filters, etc.

Quantifying Amounts, Spatial Localization, and/or Time-Dependent Response

The method also includes the step of quantifying one or more of an amount, spatial localization, and/or time-dependent response of the NAD(P)H, FAD, and/or collagen utilizing the optical response. The terminology "amount" may further describe a molar amount, a weight percent, a concentration, and/or a volume percent, and/or as described above relative to "quantification".

The terminology "spatial location" may further describe a location in x-, y-, and/or z-coordinates of one or more of the NAD(P)H, the FAD, and/or the collagen in and/or around the one or more cells. The location of one or more of these compounds may be further defined as interior and/or exterior to one or more cells. Alternatively, the spatial location may be further defined as in a spatial location of cell mitochondria and/or cell nuclei.

The terminology "time-dependent response" may be further defined as a tissue dynamic response, or time-resolved fluorescence decay. Whereas a time-integrated response reports information on an amount of fluorophores, a time-dependent response typically reflects the tissue microenvironment. This microenvironment includes, but is not limited to, the local sample pH, oxygenation, temperature, or local binding status of one or multiple fluorophores. The time-dependent response may be further identified as detected fluorescence with temporal resolution of at least 250 ps. In one embodiment, time-dependent response is measured using fluorescence lifetime imaging microscopy (FLIM) In various other embodiments, the step of quantifying may be further defined, as described below.

Quantifying an Amount of NAD(P)H Via Measurement of Fluorescence

In one embodiment, the step of quantifying is further defined as quantifying an amount of NAD(P)H via a measurement of fluorescence. The fluorescence can be measured using any method known in the art. For example, fluorescence may be measured as described above. Alternatively, second harmonic generation and FAD fluorescence measurements may be utilized to identify collagen and keratin background regions of the at least one cell. In addition, the step of quantifying may include the step of utilizing various techniques such as Markov random field denoising. Moreover, the step of quantifying may include the step of averaging over pixels after excluding the collagen and keratin background regions.

In various non-limiting embodiments, the method includes one or more steps, compounds, chemistries, and/or techniques as described in one or more of A. A. Heikal, "Intracellular coenzymes as natural biomarkers for metabolic activities and mitochondrial anomalies," Biomarkers in Medicine 4(2), 241-263 (2010); A. A. Heikal and Q. R. Yu, "Two-photon autofluorescence dynamics imaging reveals sensitivity of intracellular NADH concentration and conformation to cell physiology at the single-cell level," Journal of Photochemistry and Photobiology B—Biology 95(1), 46-57 (2009); L. C. Chen, W. R. Lloyd, S. Kuo, C. L. Marcelo, S. E. Feinberg and M. A. Mycek, "Label-free multiphoton fluorescence imaging monitors metabolism in living primary human cells used for tissue engineering," Imaging, Manipulation, and Analysis of Biomolecules, Cells, and Tissues X 8225-18 ((2012); L. C. Chen, W. R. Lloyd, S. Kuo, C. L. Marcelo, S. E. Feinberg and M. A. Mycek, "Nonlinear optical molecular imaging enables metabolic redox sensing in tissue-engineered constructs," Molecular Imaging III 8089 ((2011), each of which is expressly incorporated herein by reference in its entirety in one or more non-limiting embodiments.

Quantifying an Amount of FAD Via Measurement of Fluorescence

In another embodiment, the step of quantifying is further defined as quantifying an amount of FAD via a measurement of fluorescence. The fluorescence can be measured using any method known in the art. For example, fluorescence may be measured as described above. Alternatively, second harmonic generation and NAD(P)H fluorescence measurements are utilized to identify collagen and keratin background regions. In addition, the step of quantifying may include the step of utilizing various techniques such as Markov random field denoising. Moreover, the step of quantifying may include the step of averaging over pixels after excluding the collagen and keratin background regions.

In various embodiments, to image into a thick tissue with high scattering, non-descanned photomultipliers with bandwidths corresponding to NAD(P)H and FAD emissions can be employed to detect fluorescence images, while an internal photomultiplier set with a narrow bandwidth can be employed to detect an SHG image. Laser power can be kept constant for quantitative redox analysis and can be control at a low level. The low level laser power, after multiple measurements, may not affect cell viability (e.g. construct viability) and thus preserve a sample for histology. Measurements may be taken over a multiple day time period and yield no negative affect on sample histology. In addition, a heated stage with CO2 control can be mounted during the measurement such that the specimen is in an environment consistent with a culturing process. For example, in various embodiments, fluorescence images can be acquired with a microscope equipped with a laser, such as a Ti:sapphire laser, for use as an excitation source. The excitation source and the emission light may be coupled through an inverted microscope with various lenses, e.g. a 40× (1.25 NA)/63× (1.4 NA) oil immersion objective lenses and a 25× water immersion objective lens (0.95 NA, 2.5 mm working distance). The heated stage, as described above, may be, for example, heated to about 37° C. with 5% CO2. Excitation, e.g. laser, power can be calibrated by a power meter before measurement to provide consistent excitation energy for each measured batch, independent of measurement day. The power at the surface plane of the specimen can be varied and may be, for example, 20 mW for dish cells and 30 mW for EVPOME constructs, to limit photobleaching and non-reversible changes occurring in the specimen. The backscattered light can be passed through a filter, such as a band pass filter, from 435 to 485 nm for NAD(P)H detection and from 500 to 550 nm for FAD detection. Emission light can be collected with short-coupling non-descanned photomultiplier tubes to increase collection efficiency, e.g. at 420 to 460 nm. Detector gain and offset can be varied or kept consistent for each measurement to avoid detector saturation. Images can be acquired in about 40 seconds with a 200 Hz line scanning speed. To reduce background noise, a line average of eight, or any other suitable value, can be employed.

Ratiometrically Analyzing Fluorescence Intensity from NAD(P)H and FAD

In another embodiment, the step of quantifying is further defined as quantifying an amount of NAD(P)H and/or FAD via ratiometric measurement of fluorescence. The fluorescence can be measured using any ratiometric method known in the art. The terminology "ratiometric" or "ratiometrically" may describe a set of techniques for constructing a simple cell viability metric based on the fluorescence from multiple individual wavelengths or wavelength bands. With at least two fluorescence wavelengths or wavelength bands, the terminology ratiometric may be further defined as a metric resulting from the addition, subtraction, multiplication, or division of such parameters to create maximum contrast between viable and non-viable samples.

In addition, the step of ratiometrically analyzing a fluorescence intensity may be performed with a pair of measurements by calculating a redox ratio. In this embodiment, redox ratio is defined as [FAD]/([NAD(P)H]+[FAD]). In yet other embodiments, redox ratio may be defined as any combination including a the addition, subtraction, multiplication, or division of [NAD(P)H] and [FAD], including but not limited to [NAD(P)H]/[FAD] or [FAD]/[NAD(P)H] at each pixel after excluding the collagen and keratin background regions. Collagen and keratin background regions may be excluded as described above, employing second harmonic generated and FAD images with Markov Random Field denoising.

In various non-limiting embodiments, the method includes one or more steps, compounds, chemistries, and/or techniques as described in one or more of R. Drezek, K. Sokolov, U. Utzinger, I. Boiko, A. Malpica, M. Follen and R. Richards-Kortum, "Understanding contributions of NADH and collagen to cervical tissue fluorescence spectra: Modeling, measurements, and implications," Journal of Biomedical Optics 6(4), 385-396 (2001); J. Pitts, R. Sloboda, K. Dragnev, E. Dmitrovsky and M.-A. Mycek, "Autofluorescence characteristics of immortalized and carcinogen-transformed human bronchial epithelial cells," Journal of Biomedical Optics 6(1), 31-40 (2001); M.-A. Mycek and B. W. Pogue, Eds., Handbook of Biomedical Fluorescence, Marcel Dekker, Inc., New York (2003); M.-A. Mycek, J. D. Pitts, R. D. Sloboda, P. K. Urayama, W. Zhong, K. H. Dragnev and E. Dmitrovsky, "Using endogenous fluorescence to probe mitochondrial function in human bronchial epithelial cells," Biophysical Journal 82(1), 433a (2002); K. Moharamzadeh, I. M. Brook, R. Van Noort, A. M. Scutt, K. G. Smith and M. H. Thornhill, "Development, optimization and characterization of a full-thickness tissue engineered human oral mucosal model for biological assessment of dental biomaterials," Journal of materials science Materials in medicine 19(4), 1793-1801 (2008); J. W. Haycock, "3D cell culture: a review of current approaches and techniques," Methods in molecular biology (Clifton, N J) 695 (1-15 (2011); M. Chandra, R. H. Wilson, W.-L. Lo, K. Vishwanath, K. Izumi, S. E. Feinberg and M.-A. Mycek, "Sensing metabolic activity in tissue engineered constructs," Proc. SPIE 6628 (66280B (2007); M. Chandra, K. Vishwanath, G. D. Fichter, E. Liao, S. J. Hollister and M.-A. Mycek, "Quantitative molecular sensing in biological tissues: an approach to non-invasive optical characterization," Optics Express 14(13), 6157-6171 (2006); B. Chance, B. Schoener, R. Oshino, F. Itshak and Y. Nakase, "Oxidation-reduction ratio studies of mitochondria in freeze-trapped samples," Journal of Biological Chemistry 254(11), 4764-4771 (1979); R. Dittmar, E. Potier, M. van Zandvoort and K. Ito, "Assessment of cell viability in three-dimensional scaffolds using cellular auto-fluorescence," Tissue engineering Part C, Methods 18(3), 198-204 (2012); J. R. Lakowicz, Principles of Fluorescence Spectroscopy, Springer, New York (2006); and/or E. Dimitrow, I. Riemann, A. Ehlers, M. J. Koehler, J. Norgauer, P. Elsner, K. Konig and M. Kaatz, "Spectral fluorescence lifetime detection and selective melanin imaging by multiphoton laser tomography for melanoma diagnosis," Experimental dermatology 18(6), 509-515 (2009), each of which is expressly incorporated herein by reference in its entirety in one or more non-limiting embodiments.

Calculating a Redox Ratio of NAD(P)H and FAD

The step of quantifying may alternatively be further defined as calculating a redox ratio (RR) of NAD(P)H and FAD. For example, metabolic function may be assessed via NAD(P)H and FAD fluorescence images of the at least one cell, e.g. keratinocytes in a monolayer. As a further example, one or more cells may exhibit high NAD(P)H fluorescence around nuclei but low FAD fluorescence such that the cells would exhibit a low redox ratio (RR) (Redox Ratio=[FAD]/([NAD(P)H]+[FAD])). In one embodiment, a redox ratio map is utilized for the at least one cell. In another embodiment, keratin and collagen background signals are excluded from the redox ratio analysis by use of one or more image processing algorithms. An average redox ratio for each image can then be calculated. In one embodiment, the result shows that the redox ratio distinguishes stressed cells from control cells wherein the stressed cells exhibit a higher redox ratio value.

In various embodiments, mitochondrial autofluorescence variations can be utilized to quantify relative local metabolic rate of the one or more cells through analysis of en-face fluorescence images. The redox ratio can provide a quantitative means of comparison between measured samples. A lower redox ratio typically corresponds to lower FAD fluorescence and higher NAD(P)H fluorescence, indicating a higher cellular metabolic rate. For a tissue construct, en-face images typically include highly fluorescent structural proteins such as collagen or keratin, both common components of biological tissues and fluorescing in the regime of both NAD(P)H and FAD. Each en-face image can be processed prior to calculating the redox ratio to exclude pixels containing collagen or keratin fluorescence. Once removed, an average redox ratio at each site can then be calculated to assess local cellular metabolism.

In additional embodiments, autofluorescence images from NAD(P)H and FAD channels are employed to derive a construct redox ratio map for both cross-sectional and en-face fluorescence images, e.g. of a three-layer EVPOME structure. The health and viability of the cells can be determined by a cellular layer, which typically has a lower redox ratio than the keratin and dermal equivalent layers. Comparing a control cell to a stressed cell may demonstrate that the control cell has a lower redox ratio than the stressed cell, corresponding to increased cellular metabolic rate and higher cell viability. Both cross-sectional and en-face redox ratio maps can be calculated for analysis. Cross-sectional redox ratio maps can be sufficient for analyzing living cell layer thickness and an approximate redox ratio, but typically do not image individual cells. Therefore, en-face images can be measured to analyze individual cellular redox ratios.

The interface between the cellular and the dermal equivalent layers tends to be irregular. Therefore, each en-face image collected from the living cell layer may also include background fluorescence from a dermal equivalent layer. This dermal equivalent layer fluorescence can be localized with second harmonic generation images, employed to remove background fluorescence post-measurement, thereby isolating keratinocyte fluorescence. Keratinocyte fluorescence can be shown through two en-face autofluorescence images, one each for NAD(P)H and FAD, to create an en-face redox ratio map. Removing dermal equivalent layer fluorescence can decrease the redox ratio map resolution. However, various numbers of keratinocytes in the upper layer and a number of keratinocytes in the basal layer can be used to compute an average redox ratio for each image. Each cell layer can have a different cell density, resulting in unequal cell numbers to compute the redox ratio.

In one embodiment, the redox ratio distinguishes stressed cells from control cells by a higher value in the stressed cells than in the control cells. The difference between stressed versus control redox ratio values can be, for example, about 0.12 (95% CI=(0.11, 0.13)) after adjusting for the correlation of three sites sampled per cell under each stressed and control condition from the cells of the same patient.

In additional embodiments, cells can be evaluated to determine glucose consumption, using any method known in the art. Similarly, cells with low redox ratios may correspond to high glucose consumption and high metabolic activity, generally indicating high viability. In addition, high viability of cells with high glucose consumption and low redox ratios may also be consistent with Fourier cellular organization analysis, from which only control cells may have an average Hurst parameter greater than 0.5, indicating a well organized cellular or tissue structure.

In various non-limiting embodiments, the method includes one or more steps, compounds, chemistries, and/or techniques as described in one or more of G. M. Fitzmaurice, N. M. Laird and J. H. Ware, Applied Longitudinal Analysis, 2nd Edition, John Wiley & Sons (2011); J.-F. Gouyet, Physics and fractal structures, Masson; Springer, Paris New York (1996); and/or J. M. Levitt, M. Hunter, C. Mujat, M. McLaughlin-Drubin, K. Munger and I. Georgakoudi, "Diagnostic cellular organization features extracted from autofluorescence images," Optics Letters 32(22), 3305-3307 (2007), each of which is expressly incorporated herein by reference in its entirety in one or more non-limiting embodiments.

Quantifying an En-Face Non-Linear Optical Microscopy Spatial Image

The step of quantifying may be alternatively described as quantifying or generating an en-face non-linear optical microscopy spatial image from a NAD(P)H fluorescence image. The step of generating an en-face spatial image may be further defined as applying an image processing algorithm. The image processing algorithm may be chosen from image denoising/enhancement, background removal, fractal analysis, and combinations thereof. In one embodiment, spatial Fourier analysis is employed to characterize the at least one cell, e.g. a basal layer of an EVPOME construct. A Hurst parameter, relating to the sample's degree of order (i.e. fractal dimension), may then be extracted from each selected region.

For example, an NAD(P)H image may be split into sub-images, e.g. 4×4 or 8×8 sub-images. Image pre-processing can then be performed with a median filter, e.g. 3×3, to reduce noise while preserving edges between cellular structures, e.g. cytoplasm, nuclei, and extracellular components. Some pixels with second harmonic generation signals can then be removed with the same procedure as described above. A binary image can then be created, e.g. by setting pixels with intensity greater than the average of all non-zero pixels to 1 and all others to 0. Sub-binary images with total pixel counts greater than 40% of total pixel counts of the whole image when all pixels are 1 can then be analyzed. A PSD map in the logarithm scale can then be obtained from each sub binary image. A 5×5 mean filter can then be applied to the PSD map. To quantify the PSD characteristics, radial angle-averaged PSD values (0) can be calculated and plotted over spatial frequency (K) in the logarithm scale. In the spatial frequency range of 0.14-0.5 $\mu m^{-1}$, the PSD curve can reveal the inverse power law $\phi_K \alpha \kappa^{-\alpha}$ and can be linearly fitted to extract the corresponding power exponent (a). A Hurst parameter (H) can then be derived with the equation of $\frac{1}{2}(\alpha^{-1})$.

Cellular organization analyzed using Fourier analysis with NAD(P)H fluorescence images can show that keratinocytes are closely packed together. In a three layer construct, as described above, these cells can proliferate and differentiate to an upper layer (towards the keratin layer), wherein keratinocytes can become more loosely packed with irregular cellular organization. Both control and stressed cells can exhibit irregular cellular organization in an upper layer. However, in a basal layer, keratinocytes can be more organized in the control cells than in the stressed cells.

En-face fluorescence images can be acquired by optically sectioning cells, guided by cross-sectional images, e.g. to measure image planes that are preferentially closer to the upper layer or the basal layer. En-face images can show cellular organization with NAD(P)H and FAD fluorescence. Quantitative analysis of the en-face fluorescence images can be employed to extract cellular organization information and tissue metabolism from control and thermally stressed cells.

In various non-limiting embodiments, the method includes one or more steps, compounds, chemistries, and/or techniques as described in one or more of R. Drezek, K. Sokolov, U. Utzinger, I. Boiko, A. Malpica, M. Follen and R. Richards-Kortum, "Understanding contributions of NADH and collagen to cervical tissue fluorescence spectra: Modeling, measurements, and implications," Journal of Biomedical Optics 6(4), 385-396 (2001); J. Pitts, R. Sloboda, K. Dragnev, E. Dmitrovsky and M.-A. Mycek, "Autofluorescence characteristics of immortalized and carcinogen-transformed human bronchial epithelial cells," Journal of Biomedical Optics 6(1), 31-40 (2001); M.-A. Mycek and B. W. Pogue, Eds., Handbook of Biomedical Fluorescence, Marcel Dekker, Inc., New York (2003); J. W. Haycock, "3D cell culture: a review of current approaches and techniques," Methods in molecular biology (Clifton, N J) 695 (1-15 (2011); R. Dittmar, E. Potier, M. van Zandvoort and K. Ito, "Assessment of cell viability in three-dimensional scaffolds using cellular auto-fluorescence," Tissue engineering Part C, Methods 18(3), 198-204 (2012); I. Georgakoudi, W. L. Rice, M. Hronik-Tupaj and D. L. Kaplan, "Optical spectroscopy and imaging for the noninvasive evaluation of engineered tissues," Tissue Eng Part B Rev 14(4), 321-340 (2008); B. G. Wang, K. Konig and K. J. Halbhuber, "Two-photon microscopy of deep intravital tissues and its merits in clinical research," Journal of microscopy 238(1), 1-20 (2010); and/or Y. C. Wu, P. Xi, J. A. Y. Qu, T. H. Cheung and M. Y. Yu, "Depth-resolved fluorescence spectroscopy reveals layered structure of tissue," Optics Express 12(14), 3218-3223 (2004), each of which is expressly incorporated herein by reference in its entirety in one or more non-limiting embodiments.

Quantifying a Cross-Sectional Optical Image from NAD(P)H Fluorescence

In another embodiment, the step of quantifying and/or generating the cross-sectional optical image includes or is further defined as line scanning along an axial direction to optically section the at least one cell. For example, the at least one cell may be further defined as a tri-layer (engineered) tissue comprising a top keratin layer, a middle living cell layer, and a bottom dermal equivalent layer, and the step of quantifying the thickness may be further defined as measuring a thickness between the top keratin layer and the bottom dermal equivalent layer. For accurate calculation of layer thickness, a measurement may be estimated at locations that are representative of an overall construct cell layer growth.

Quantifying a Time-Dependent Response Employing Fluorescence Lifetime Imaging Microscopy (FLIM)

In still other embodiments, fluorescence-lifetime imaging microscopy (FLIM) images are analyzed with exponential fitting and phasor analysis by extracting time-resolved fluorescence decays either from individual cells (e.g. monolayer samples) or regions absent of second harmonic generation signal (e.g. EVPOMEs). Fluorescence-lifetime imaging microscopy is an imaging technique for producing an image based on the differences in the exponential decay rate of the fluorescence from a fluorescent sample. It can be used as an imaging technique in confocal microscopy, wide-field single photon microscopy, two-photon excitation microscopy, and multiphoton tomography. The decay behavior of the fluorophore signal, rather than its intensity, is typically used to create the image contrast in FLIM. This typically has the advantage of minimizing the effect of photon scattering in thick layers of a sample as compared to intensity imaging.

For example, after extracting a time-resolved decay, a mathematical model can then be employed to characterize the decay with both a bi-exponential decay model and a phasor analysis algorithm. Prior to phasor analysis, each fluorescence decay can be shifted prior to transformation so that the fluorescence peak is at time=0. In addition, extracted fluorescence decays can be best-fit to a two-exponential model. Fitting can be performed with an iterative least-squares model, e.g. employing SymPhoTime analysis software. An instrument response function (IRF) can be deconvolved with the model, measured as the SHG emission from a collagen sample. Fitting parameters can include up to four lifetime parameters and their corresponding amplitudes, intensity background correction, IRF time shift, and IRF intensity background correction. In one embodiment, two lifetime fitting parameters are employed. Moreover, free NAD(P)H can exhibit a short lifetime ($\tau 2$) while bound NAD(P)H can exhibit a long(er) lifetime ($\tau 1$). Alternatively, bound FAD can exhibit a short lifetime ($\tau 2$) while free FAD can exhibit a long(er) lifetime ($\tau 1$). In addition, a difference between stressed and non-stressed cells in an NAD(P)H channel may be that there may be a greater percent contribution from bound NAD(P)H in stressed cells, e.g. keratinocytes, compared to non-stressed cells. Similarly, a difference between stressed and non-stressed cells in the FAD channel may be that there is a greater percent contribution from free FAD in non-stressed (control) cells compared to stressed cells.

Resolving Fluorescence Decay Measurements to Quantify Bound-NAD(P)H Contributions to Fluorescence Lifetime The step of quantifying may be further defined as resolving fluorescence decay measurements to quantify bound-NAD(P)H contributions to fluorescence lifetime. In one embodiment, the step of resolving includes selecting two collagen-free regions of NAD(P)H fluorescence that are void of background collagen fluorescence and that have at least 100 photon counts in a peak channel. Typically, the terminology "void of background collagen fluorescence" describes a region that is identified as having no visible second harmonic generated signal in pixels defined within a region of an FLIM image to analyze. In another embodiment, the method further includes the step of applying a least-squares iterative fit with a double exponential model to extract individual and average lifetimes and total contribution of a slow lifetime component. For example, the slow lifetime component of NAD(P)H fluorescence may be attributed to bound-NAD(P)H. In still another embodiment, the total contribution is further defined as a contribution from bound-NAD(P)H and has a lifetime of from 1 to 4, 1.1 to 3.9, 1.2 to 3.8, 1.3 to 3.7, 1.4 to 3.6, 1.5 to 3.5, 1.6 to 3.4, 1.7 to 3.3, 1.8 to 3.2, 1.9 to 3.1, 2 to 3, 2.1 to 2.9, 2.2 to 2.8, 2.3 to 2.7, 2.4 to 2.6, or about 2.5, nanoseconds, which may change depending on a studied sample.

In various non-limiting embodiments, the method includes one or more steps, compounds, chemistries, and/or techniques as described in one or more of M.-A. Mycek and B. W. Pogue, Eds., Handbook of Biomedical Fluorescence, Marcel Dekker, Inc., New York (2003); M. Chandra, K. Vishwanath, G. D. Fichter, E. Liao, S. J. Hollister and M.-A. Mycek, "Quantitative molecular sensing in biological tissues: an approach to non-invasive optical characterization," Optics Express 14(13), 6157-6171 (2006); J. R. Lakowicz, Principles of Fluorescence Spectroscopy, Springer, New York (2006); C.-W. Chang, D. Sud and M.-A. Mycek, "Fluorescence lifetime imaging microscopy," in Methods in Cell Biology G. Sluder and D. Wolf, Eds., Elsevier Inc (2007); W. R. Lloyd, L.-C. Chen, S. Kuo, C. L. Marcelo, S. E. Feinberg and M.-A. Mycek, "Fluorescence lifetime imaging microscopy (FLIM) studies of living primary human cells for applications in tissue regeneration," Proceedings of the SPIE 8226 (82260E-82266 (2012); M. C. Skala, K. M. Riching, A. Gendron-Fitzpatrick, J. Eickhoff, K. W. Eliceiri, J. G. White and N. Ramanujam, "In vivo multiphoton microscopy of NADH and FAD redox states, fluorescence lifetimes, and cellular morphology in precancerous epithelia," Proc Natl Acad Sci USA 104(49), 19494-19499 (2007); C. Stringari, A. Cinquin, O. Cinquin, M. A. Digman, P. J. Donovan and E. Gratton, "Phasor approach to fluorescence lifetime microscopy distinguishes different metabolic states of germ cells in a live tissue," Proceedings of the National Academy of Sciences of the United States of America 108(33), 13582-13587 (2011); and/or M. A. Mycek, P. Urayama, W. Zhong, J. A. Beamish, F. K. Minn, R. D. Sloboda, K. H. Dragnev and E. Dmitrovsky, "A UV-visible-NIR fluorescence lifetime imaging microscope for laser-based biological sensing with picosecond resolution," Applied Physics B—Lasers and Optics 76(5), 483-496 (2003), each of which is expressly incorporated herein by reference in its entirety in one or more non-limiting embodiments.

Resolving Fluorescence Decay Measurements to Quantify NAD(P)H Average Fluorescence Lifetimes The step of quantifying may be further defined as resolving fluorescence decay measurements to quantify NAD(P)H average fluorescence lifetimes. In one embodiment, the step of resolving includes selecting two collagen-free region of NAD(P)H fluorescence void of background collagen fluorescence, as described above, and having at least 100 photon counts in a peak channel. In another embodiment, the method further includes the step of applying a least-squares iterative fit with a double exponential model to extract individual and average lifetimes and total contribution of a slow lifetime component. Here, the average fluorescence lifetime of NAD(P)H may be calculated with the extracted fitting parameters from the iterative fit, which may include the slow and fast lifetime components and their amplitude contributions. In still another embodiment, the average lifetime is further defined the average fluorescence decay rate from NAD(P)H and has a lifetime of from 1 to 4, 1.1 to 3.9, 1.2 to 3.8, 1.3 to 3.7, 1.4 to 3.6, 1.5 to 3.5, 1.6 to 3.4, 1.7 to 3.3, 1.8 to 3.2, 1.9 to 3.1, 2 to 3, 2.1 to 2.9, 2.2 to 2.8, 2.3 to 2.7, 2.4 to 2.6, or about 2.5, nanoseconds, which may change depending on a studied sample.

In various non-limiting embodiments, the method includes one or more steps, compounds, chemistries, and/or techniques as described in one or more of C.-W. Chang, D. Sud and M.-A. Mycek, "Fluorescence lifetime imaging microscopy," in Methods in Cell Biology G. Sluder and D. Wolf, Eds., Elsevier Inc (2007); W. R. Lloyd, L.-C. Chen, S. Kuo, C. L. Marcelo, S. E. Feinberg and M.-A. Mycek, "Fluorescence lifetime imaging microscopy (FLIM) studies of living primary human cells for applications in tissue regeneration," Proceedings of the SPIE 8226 (82260E-82266 (2012); and/or M. C. Skala, K. M. Riching, A. Gendron-Fitzpatrick, J. Eickhoff, K. W. Eliceiri, J. G. White and N. Ramanujam, "In vivo multiphoton microscopy of NADH and FAD redox states, fluorescence lifetimes, and cellular morphology in precancerous epithelia," Proc Natl Acad Sci USA 104(49), 19494-19499 (2007), each of which is expressly incorporated herein by reference in its entirety in one or more non-limiting embodiments.

Resolving Fluorescence Decay Measurements to Quantify Free FAD Contributions to Fluorescence Lifetime The step of quantifying may alternatively be described as resolving fluorescence decay measurements to quantify free FAD contributions to fluorescence lifetime. For example, the step of resolving may include selecting two collagen-free region of FAD fluorescence void of background collagen fluorescence, as described above, and having at least 100 photon counts in a peak channel. The method may also include the step of applying a least-squares iterative fit with a double exponential model to extract individual and average lifetimes and total contribution of a slow lifetime component. Here, the slow lifetime component of FAD fluorescence may be attributed to free-FAD. Moreover, the total contribution is further defined as a contribution from free FAD and has a lifetime of from 1 to 4, 1.1 to 3.9, 1.2 to 3.8, 1.3 to 3.7, 1.4 to 3.6, 1.5 to 3.5, 1.6 to 3.4, 1.7 to 3.3, 1.8 to 3.2, 1.9 to 3.1, 2 to 3, 2.1 to 2.9, 2.2 to 2.8, 2.3 to 2.7, 2.4 to 2.6, or about 2.5, nanoseconds, which may change depending on a studied sample.

It is contemplated that any one or more of the aforementioned embodiments of quantifying may be combined with any one or more other embodiments of quantifying. For example, the step of quantifying may be further defined as, or include, one or more of the steps described above.

Additional Embodiments

In one additional embodiment, a keratinocyte layer of a tissue layer is interrogated to determine tissue metabolic activity. For example, metabolic redox sensing may utilize endogenous fluorescence from NAD(P)H and FAD to create a redox ratio, which noninvasively and quantitatively assesses cell and tissue viability. However, the keratin and collagen that exists within an EVPOME, for example, can cause additional absorption, scattering, and fluorescence of incident photons. These phenomena can serve as unwanted background and impact the signal from the keratinocyte layer, resulting in signal mixing and poor image resolution, e.g. with single photon excitation. To overcome this difficulty, two-photon nonlinear optical imaging can be employed. With the benefits of deep photon penetration depth and fine optical sectioning (<1 μm), excitation and hence detection of the keratin and collagen layers can be largely avoided. Furthermore, nonlinear optical imaging can provide useful second harmonic generation (SHG) signals from collagen, enabling preferential exclusion of the collagen contents from fluorescence images by post processing.

In one or more additional embodiments, the step of quantifying may be further defined as any one or more of the following:

I. Employing nonlinear optical microscopy to noninvasively section a single layer of cells (about <1 μm thick) and measure an en-face image of cells, e.g. keratinocytes, in dish samples and EVPOMEs or other cells. For example, primary human keratinocytes may be evaluated with fluorescence imaging and/or EVPOMEs may be evaluated with fluorescence imaging and second harmonic generation images.

II. Utilizing cross-sectional optically sectioned images of cells, e.g. EVPOME three-layered structures, compared with corresponding histology slides. For example, cross-sectional images of an EVPOME's three-layered structure may be examined and used to determine morphological spatial relationships between the layers, thereby identifying dissociated layers.

III. Analyzing en-face fluorescence images by computing the redox ratio. For example, redox ratios can be used to characterize cellular metabolism of cells, e.g. primary human keratinocytes, in dish samples and EVPOMEs or other cells. The redox ratio method may quantitatively distinguish thermally-stressed cells from non-compromised cells with statistical significance.

IV. Analyzing en-face fluorescence images with spatial Fourier analysis to assess a cell's basal cellular layer organization. For example, this step may quantitatively distinguish thermally stressed cells from non-compromised cells with statistical significance.

V. Utilizing Fourier analysis and redox ratio map analysis of cells, e.g. EVPOMEs, in patient independent techniques to determine results of multiple cells, e.g. EVPOMEs made with keratinocytes, from different patients and distinguish thermally-stressed cells from non-compromised cells with statistical significance.

VI. Utilizing fluorescence lifetime images acquired from en-face fluorescence images and analyzing the images with one or more mathematical methods, e.g. with bi-exponential decay and/or phasor analysis algorithms.

In another example embodiment, a measurement scheme of in vitro keratinocytes steady-state fluorescence is shown in the Table below wherein, for each batch, two samples are cultured. One may be cultured according to a control protocol and the second according to a stressed protocol. For each sample, two or more sites can be randomly selected for measurement. For each site, numerous (e.g. fifteen) cells can be randomly selected to calculate an average redox ratio, resulting in numerous (e.g. thirty) analyzed cells for each sample.

|  | Patient (Batch) | | | |
|---|---|---|---|---|
|  | 1 | 2 | 3 | 4 |
| Culture Condition | P | P | D | D |
| Dish | 2 dishes: 1 control + 1 stressed | 2 dishes: 1 control + 1 stressed | 2 dishes: 1 control + 1 stressed | 2 dishes: 1 control + 1 stressed |
| Site | 2 sites | 2 sites | 2 sites | 2 sites |
| Cell | 15 cells | 15 cells | 15 cells | 15 cells | wherein P signifies proliferation and D signifies differentiation.

In another embodiment, in vitro keratinocytes fluorescence lifetime imaging (FLIM) measurements are gathered as set forth in the Table below wherein data may be included from numerous, e.g. four, batches. For example, a varying number of cells can be analyzed from each batch based on a number of sites measured and the number of cells at each site. At sites with numerous cells, 10-15 cells, for example, can be randomly selected for analysis by both exponential fitting and phasor analysis.

| NAD(P)H | | | | | |
|---|---|---|---|---|---|
|  | Patient | | | | |
|  | 1 | 1 | 2 | 2 | 4 |
| Measurement Day | 1 | 2 | 1 | 2 | 1 |
| Culture Condition | D | D | D | D | D |
| Dish(es) | 1 Dish: 1 Control | 2 Dishes: 1 Control + 1 Stressed | 1 Dish: 1 Control | 2 Dishes: 1 Control + 1 Stressed | 2 Dishes: 1 Control + 1 Stressed |
| Site(s) | 3 Sites: 3 Control | 3 Sites: 1 Control + 1 Stressed | 3 Sites: 3 Control | 4 Sites: 2 Control + 3 Stressed | 3 Sites: 2 Control + 2 Stressed |
| Cell(s) | 28 Control | 13 Control + 14 Stressed | 45 Control | 22 Control + 33 Stressed | 22 Control + 24 Stressed |

| FAD | | |
|---|---|---|
|  | Patient | |
|  | 3 | 4 |
| Culture Condition | D | D |
| Dish(es) | 1 Dish: 1 Control | 2 Dishes: 1 Control + 1 Stressed |
| Site(s) | 6 Sites: 3 Control + 3 Stressed | 4 Sites: 2 Control + 2 Stressed |
| Cell(s) | 37 Control + 50 Stressed | 22 Control + 22 Stressed | wherein D signifies differentiation.

In another embodiment, two EVPOMEs are cultured, one control and one thermally stressed on day 9. For each EVPOME, three sites are randomly selected to measure fluorescence from the living cell layer (LC). For each site, two cellular layers are imaged to analyze: an upper layer close to the keratin layer (K) and a lower layer close to the dermal equivalent (DE), wherein D signifies differentiation.

|  | Patient (Batch) | | |
|---|---|---|---|
|  | 1 | 2 | 3 |
| Culture Condition | 2 EVPOMEs: 1 control + 1 stressed | 2 EVPOMEs: 1 control + 1 stressed | 2 EVPOMEs: 1 control + 1 stressed |
| EVPOME Site | 3 sites | 3 sites | 3 sites |
| Depth | 2 depths: Close to K + close to DE | 2 depths: Close to K + close to DE | 2 depths: Close to K + close to DE |
| Cell | Close to K: 10-15 cells Close to DE: 20-40 cells | Close to K: 10-15 cells Close to DE: 20-40 cells | Close to K: 10-15 cells Close to DE: 20-40 cells |

In yet another embodiment, in vitro keratinocytes are evaluated to determine fluorescence intensity images. In still another embodiment, the following experimental parameters are utilized:

| Microscope model | Leica TCS SP5 |
|---|---|
| Objective lens | 25x water immersion with 2 mm working distance for EVPOME |
|  | 40/63x oil immersion for dish cells |
| Power | 30 mW for EVPOME |
|  | 20 mW for dish cells |
| Detectors | An internal tunable PMT for SHG images |
| Excitation/ NAD(P)H | 705 nm/435-485 nm |
| Detection FAD | 900 nm/500-550 nm |
| Wavelength Collagen | 880 nm/420-460 nm |

In other embodiments, the following parameters are utilized for keratinocytes/EVPOME FLIM measurements: Microscope model: Leica TCS SPS, Objective Lens: 40/63× oil immersion, ~20 mW Externalnon-descanned PMTs, NAD(P)H emission/detection: 705 nm/400-500 nm, FAD emission/detection: 900 nm/500-600 nm, laser repetition rate: 100 fs, Temporal Resolution: 4 ps.

In still another embodiment, FLIM images are analyzed with exponential fitting and phasor analysis by extracting time-resolved fluorescence decays from individual cells. After extracting a time-resolved decay, a mathematical model can be employed to characterize the decay with both a bi-exponential decay model and a phasor analysis algorithm. For example, between 5 and 15 cells can be selected per image based on cell density and number of cells in each image. More specifically, from a full image an individual cell can be isolated by selecting a region of interest. All individual pixels can be summed across x and y space, resulting in a single one time-resolved fluorescence decay image representative of that cell.

This image can be further analyzed by employing two-exponential fitting or phasor analysis. For example, using a bi-exponential model, each extracted decay image can be fit with a least-squares bi-exponential model, e.g. utilizing SymPhoTime (Picoquant GmbH, Germany), to the equation: $F_{model}(t) = a_1 \exp(-t/\tau_1) + a_2 \exp(-t/\tau_2)$. Moreover, models can be fit in a contained fitting window, starting just prior to the rising edge of the fluorescence signal and ending after about 95% of the decay is completed. Subsequently, a common IRF can be deconvolved with each fluorescence decay, measured as the SHG response from a collagen sample.

In still another embodiment, using phasor analysis, fluorescence decays can be transformed and modeled with the equations:

$$g(\omega) = \int F(t)\cos(\omega t)dt / \int F(t)dt = m \cos(\theta)$$

$$s(\omega) = \int F(t)\sin(\omega t)dt / \int F(t)dt = m \sin(\theta)$$

wherein $\omega$ is the harmonic frequency of the fluorescence decay (e.g. $\omega = 80$ MHz.), $m = (g^2 + s^2)^{1/2}$ is the magnitude, and $\theta = \tan^{-1}(s/g)$ is the phase. Phasor analysis can be utilized to directly transform fluorescence decay into a frequency domain, exhibiting the parameters g and s. For example, each fluorescence decay can be shifted prior to transformation so that the fluorescence peak is at time=0. Based on transform equations of g and s, single exponential fluorescence decays can be transformed to lie on a semicircle of a polar (phasor) plot. Alternatively, fluorescence decays with more than one component may lie within the semicircle. Fluorescence decays with longer average lifetimes may appear closer to the plot origin.

In additional embodiments, fluorescence redox sensing can be applied, e.g. to dish samples with four metabolic rates, corresponding to four culture conditions: control proliferating, stressed proliferating, control differentiating, and stressed differentiating. As just one example, proliferating keratinocytes, or any suitable cells, can be cultured in a low-calcium medium to form a cellular monolayer. Differentiating keratinocytes, or any suitable cells, can be cultured in, and stimulated by, a higher-calcium medium to form a three-dimensional layered structure. Proliferating cells with control culture conditions can be spatially separated, whereas differentiating cells with control culture conditions can be crowded together. Furthermore, proliferating cells typically have higher redox ratios than differentiating cells under control culture conditions.

In additional embodiments, thermal stress can be applied to any suitable cells. In these embodiments, the redox ratios of the stressed cells tend to be higher than the redox ratios of the control cells, as typically exhibited by higher FAD fluorescence and lower NAD(P)H fluorescence. Proliferating keratinocytes tend to have inconsistent redox ratios, indicating high cellular metabolic variability. Stressed differentiating keratinocytes also tend to exhibit higher redox ratios than control keratinocytes. The increased redox ratio from control to stressed differentiating keratinocytes and the variability between the redox ratio of stressed cells tend to be relatively small compared to those of the proliferating cells. As just one example, the differentiating keratinocytes may resist adverse thermal conditions as compared to proliferating keratinocytes.

In additional embodiments, fluorescence intensity differences in cells or cellular layers of measured EVPOMEs can directly relate to the metabolic rate of the cells/tissue, thereby enabling quantification of cell viability. For example, a control cell may exhibit a higher NAD(P)H fluorescence than a stressed cell. Conversely, a stressed cell may exhibit higher cellular FAD fluorescence than a control cell. This NAD(P)H and FAD variation can be attributed to changes in tissue metabolic rates in the cells.

Statistical Significance

The method may also include the step of determining the statistical significance of one or more data generated from the method of this disclosure. For example, stressed and control cells, e.g. EVPOMEs, can be evaluated from a single batch, e.g. patient. For example, analyses on multiple batches can be done using one-sample t-tests. For one sample t-tests, a within-batch difference of each extracted parameter (e.g. H and redox ratio) between a pair of stressed and control EVPOMEs cam be calculated. This difference can be expressed as a percent relative to the control sample parameter, and the mean percent difference can be compared with zero value.

Alternate statistical approaches can also be used. For example, non-parametric Wilcoxon rank tests and a test based on fitting a linear mixed-effects model can be used. The non-parametric tests can be employed due to small sample sizes for patient level data analysis. Alternatively, site level data can be analyzed using the linear mixed-effects models. The site level data tends to utilize much larger sample sizes, but the analysis typically must account for within-patient correlation of multiple sites sampled per EVPOME under both stressed and control conditions. For example, for the analysis of dish data, the mixed-effects model used patient, dish and sites as random intercepts to account for the correlation among values within dishes, dishes within patient, and sites within dishes. Using these models, any differences associated with the differentiated versus proliferated cells or the top versus bottom layer, can be evaluated. When no differences associated with these parameters are found, these variables can be dropped from one or more models.

In still other embodiments, the method of this disclosure allows for nonlinear optical microscopy to noninvasively characterize tissue-engineered constructs with cross-sectional and en-face images. Alternatively, the method allows for quantitative analyses of images to be developed and employed to assess the viability of cells, e.g. primary human keratinocytes in dishes and in EVPOMEs. The method may alternatively allow for use of spatial Fourier analysis to distinguish multiple thermally-stressed cells, e.g. EVPOMEs, from viable cells with statistical significance (e.g. p-value <0.046). The method may also allow use of redox ratio map analysis to distinguish multiple thermally-stressed cells, e.g. EVPOMEs and keratinocytes, from viable cells with statistical significance (e.g. p-value <0.019). The method may also produce results that are comparable with histology and/or the glucose analysis/reading results. The method may also allow time-resolved fluorescence lifetime images to be analyzed by extracting individual cells thereby allowing statistically significant parameters to be extracted from both bi-exponential and phasor analysis algorithms when comparing thermally stressed and control (non-stressed) cells, e.g. keratinocytes in dish samples (from both NAD(P)H and FAD channels). Alternatively, the method allows fluorescence lifetime images and spatial Fourier analysis algorithms, or NAD(P)H/FAD fluorescence intensity images alone to be used to show the potential to only need one channel of fluorescence data to distinguish stressed from non-stressed cells, e.g. keratinocytes, as compared to two channels for redox imaging. The method may also allow nonlinear optical microscopy (e.g. steady-state intensity and fluorescence lifetime imaging) with quantitative analysis to noninvasively and quantitatively assess cell, e.g. tissue-engineered construct, viability during manufacture and/or growth and prior to implantation.

EXAMPLES

First Set of Examples

This first set of Examples is independent from the second set of examples set forth below.

In various embodiments, phasor plot analysis combined with error propagation analysis was developed to advance the applications of fluorescence lifetime imaging microscopy (FLIM). The developed algorithm was applied to label-free one-channel FLIM images from the living engineered tissue EVPOME to automatically indentify and segment different tissue constituents. The result was compared to two-channel fluorescence intensity images and a fast FLIM map.

In these embodiments, phasor analysis has the advantages of rapid and direct interpretation and visualization of FLIM images without prior knowledge of the samples. The algorithm was explored and extended to develop the phasor error analysis. Phasor error analysis quantitatively identifies the size and the shape of the uncertainty areas of the fluorescence lifetimes of interest on a phasor plot. The developed phasor error analysis algorithm was verified with biological relevant fluorophores. Multiple tissue constituents were differentiated by assessing one-channel NAD(P)H FLIM images acquired from tissue-engineered constructs with the developed phasor error analysis. The viability assessment of FLIM images acquired from tissue-engineered constructs was improved by performing phasor error analysis to exclude extracellular signals from the cellular viability assessments.

Phasor plot analysis is based on procedures developed to analyze dielectric relaxation experiments, i.e. a sample's transient responses to repeated perturbations. In fluorescence, this method was applied to analyze frequency-domain fluorescence lifetime imaging microcopy (FLIM) data, as the modulated excitation light is the perturbation and the fluorescence emission is the relaxation. Phasor analysis was further developed to offer a simple, graphical, and rapid algorithm for interpreting frequency-domain FLIM data that were obtained after single excitation frequency from samples exhibiting more than one fluorescence lifetime. In frequency-domain experiments, phasor analysis transforms the modulation, M, and the phase, φ, of the emission with respect to the excitation into $$g = M \cos \varphi \quad (1)$$

and $$s = M \sin \varphi, \quad (2)$$

A pair of g and s values represents a phasor vector on the phasor plot.

Phasor plot analysis can be adapted to analyze time-domain FLIM images. Compared to traditional exponential fitting, advantages include real-time analysis of multiple fluorophores in complex samples, such as biological samples. FLIM-FRET donor and accepter trajectory was visualized on the phasor plot. Cellular metabolism changes and differentiation stages were monitored on the phasor plot. It was further developed to analyze steady-state fluorescence spectrum to distinguish multiple species in biological samples.

Thorough analysis of such samples typically requires unbiased, quantitative assessment of contributing fluorophores and outliers. Phasor plot uncertainty through error propagation of noise in time-domain FLIM can be quantified. Uncertainty of phasor coordinates was calculated by introducing Poisson noise with modeled single exponential decays. Then, phasor analysis was employed with TCSPC-FLIM data of biologically-relevant fluorophores to successfully segment different fluorescent species in tissue-engineered constructs. Furthermore, the method assisted in assessing tissue viability by excluding unwanted signals from extracellular matrices when assessing cellular viability. Such quantitative uncertainty analysis is the first step towards automated visualization and interpretation of phasor plots.

Phasor Plot Analysis:

FLIM images are 3-dimensional, consisting of spatial (x, y) and temporal (t) information. Traditional analysis methods employ exponential fitting that is complicated and computationally expensive. Phasor plot analysis avoids complicated exponential fitting procedures and typically does not require prior knowledge of the biological samples such as number of components for the exponential fitting. Time-domain FLIM can be analyzed with phasor analysis because the excitation pulse frequency can be transformed into phasor space similarly to the sinusoidal excitation frequency of frequency domain FLIM. To provide an instantaneous (excluding complex exponential fitting procedures) view of the fluorescence decay in time-domain experiments, the frequency-domain FLIM phasor plot analysis was modified. Fluorescence decays, F(t), at each pixel of an image were transformed into a phasor domain by $$g = \frac{\int_0^\infty F(t)\cos(\omega t)dt}{\int_0^\infty F(t)dt} \quad (3)$$

and $$s = \frac{\int_0^\infty F(t)\sin(\omega t)dt}{\int_0^\infty F(t)dt}, \quad (4)$$

where ω=laser repetition angular frequency. Each pixel of the image is transformed to a point, described by the coordinates g & s on the phasor plot. If the fluorescence decay is single exponential, the coordinates g and s become $$g = \frac{1}{1 + (\omega\tau)^2} \quad (5)$$

and $$s = \frac{\omega\tau}{1+(\omega\tau)^2}. \tag{6}$$

These two coordinates lie on a semicircle of a phasor plot. If the fluorescence decay is multi-exponential, the phasor point lies inside the semicircle.

The analysis is performed by observing clustering of pixels in specific regions of the phasor plot, providing a graphical view of FLIM images. The method can also be used in a reciprocal mode in which each point of the phasor plot is mapped, and pseudocolored, to a pixel of the image. Since every molecular species has a specific phasor vector, located in specific regions, users can identify molecules by their position on the phasor plot. Therefore, the phasor plots analysis makes the interpretation of FLIM data accessible to the nonexpert.

Error Analysis of Phasor Plots:

Phasor plot analysis was applied to TCSPC-FLIM images to rapidly characterize living cells and engineered tissues. Before analyzing, FLIM images were binned to obtain sufficient signals per pixel to analyze. The binned FLIM images were transformed to the 2-dimensional phasor plots. Each binned pixel creates one point on the phasor plot, resulting in a spread of points indicating the lifetime distribution. Alternatively, error analysis assists in quantitatively selecting the regions of interest on the phasor plots.

Algorithms:

Phasor coordinates, g and s, for time-domain FLIM are defined in eqs. (3) and (4). Error propagation analysis was employed to derive $\Delta g$ and $\Delta s$ on a phasor plot. Since g is a fractional number, error propagation was calculated as $$\left(\frac{\Delta \frac{A}{B}}{\frac{A}{B}}\right)^2 = \left(\frac{\Delta A}{A}\right)^2 + \left(\frac{\Delta B}{B}\right)^2 - 2\left(\frac{\text{Cov}(A,B)}{AB}\right) \tag{7}$$

Thus,

A=numerator of $g = \int_0^\infty I(t)\cos(\omega t)dt$
B=denominator of $g = \int_0^\infty I(t)dt$ In the case in which there is the contribution of multi exponential components, $$A = \sum_i \int_0^\infty I(t)\cos(\omega t)dt$$

$$B = \sum_i \int_0^\infty I(t)dt$$

Assuming all the components are independent, and only Poisson noise is present in the TCSPC-FLIM data, $$\Delta A^2 = \sum_i \int_0^\infty \Delta I_i^2(t)\cos^2(\omega t)dt = \sum_i \int_0^\infty I_i(t)\cos^2(\omega t)dt \tag{8}$$

$$\Delta B^2 = \sum_i \int_0^\infty \Delta I_i^2(t)dt = \sum_i \int_0^\infty I_i(t)dt$$

$$\text{Cov}(A,B) = \sum_i \int_0^\infty \cos(\omega t)\text{var}(I_i(t))dt = \sum_i \int_0^\infty I_i(t)\cos(\omega t)dt = A$$

Therefore, $$g = \sqrt{\left(\frac{\sum_i \int_0^\infty I_i(t)\cos(\omega t)dt}{\sum_i \int_0^\infty I_i(t)dt}\right)^2 \times \left[\left(\frac{\sqrt{\sum_i \int_0^\infty I_i(t)\cos^2(\omega t)dt}}{\sum_i \int_0^\infty I_i(t)\cos(\omega t)dt}\right)^2 + \left(\frac{\sqrt{\sum_i \int_0^\infty (I_t)dt}}{\sum_i \int_0^\infty I_i(t)dt}\right)^2 - 2\frac{1}{\int_0^\infty I(t)dt}\right]}$$

$\Delta s$ can be derived with the same procedure, $$\Delta s = \sqrt{\left(\frac{\sum_i \int_0^\infty I_i(t)\sin(\omega t)dt}{\sum_i \int_0^\infty I_i(t)dt}\right)^2 \times \left[\left(\frac{\sqrt{\sum_i \int_0^\infty I_i(t)\sin^2(\omega t)dt}}{\sum_i \int_0^\infty I_i(t)\sin(\omega t)dt}\right)^2 \left(\frac{\sqrt{\sum_i \int_0^\infty I_i(t)dt}}{\sum_i \int_0^\infty I_i(t)dt}\right)^2 - 2\frac{1}{\int_0^\infty I(t)dt}\right]} \tag{9}$$

In addition to $\Delta g$ and $\Delta s$, the covariance of g and s was derived. A parameter P is defined as g/s.

$$P = \frac{g}{s} = \frac{\sum_i \int_0^\infty I_i(t)\cos(\omega t)dt}{\sum_i \int_0^\infty I_i(t)\sin(\omega t)dt}$$

Therefore, by following eq. (7), $$\left(\frac{\Delta P}{P}\right)^2 = \frac{\sum_i \int_0^\infty I_i(t)\cos^2(\omega t)dt}{\left(\sum_i \int_0^\infty I_i(t)\cos(\omega t)dt\right)^2} + \frac{\sum_i \int_0^\infty I_i(\tau)\sin^2(\omega t)dt}{\left(\sum_i \int_0^\infty I_i(t)\sin(\omega t)dt\right)^2} - 2\left(\frac{\cos(\omega t)\sin(\omega t)\sum_i I_i(t)}{\left(\sum_i \int_0^\infty I_i(t)\cos(\omega t)dt\right)\left(\sum_i \int_0^\infty I_i(t)\sin(\omega t)dt\right)}\right) \tag{10}$$

$\Delta P$ can also be written as $$\Delta\frac{g}{s},$$

which can be rewritten in another format, $$\left(\frac{\Delta P}{P}\right)^2 = \left(\frac{\Delta\frac{g}{s}}{\frac{g}{s}}\right)^2 = \left(\frac{\Delta g}{g}\right)^2 + \left(\frac{\Delta g}{s}\right)^2 - 2\left(\frac{\text{Cov}(g,s)}{gs}\right) \tag{11}$$

Therefore, $$\text{Cov}(g,s) = \frac{gs}{2}\left[\left(\frac{\Delta g}{g}\right)^2 + \left(\frac{\Delta s}{s}\right)^2 - \left(\frac{\Delta P}{P}\right)^2\right]$$

Substituting eqs (8), (9), and (10) into eq (11), the covariance of g and s can be derived. Δg, Δs, and Cov(g,s) (tilt) compose a covariance matrix, $$\begin{bmatrix} \Delta g^2 & \text{Cov}(g,s) \\ -\text{Cov}(g,s) & \Delta s^2 \end{bmatrix}$$

The matrix was used to transform a circle to a σ ellipse by Cholesky decomposition under the assumption that Δg and Δs approximate to the normal distribution (due to the large number of collected photons).

Phasor Error Analysis Procedures:

For a FLIM image with only one species, one cluster of phasor points was generated with points indicating a distribution of lifetimes. A simple linear fitting for those points on the phasor plot extracted two lifetimes. The two lifetimes were extracted by finding the intercepts of the fitted line and the single-exponential semicircle on the phasor plot. With the two lifetimes, error analysis then calculates Δg, Δs, and Cov(g,s), thus determining an uncertainty area.

For a FLIM image with multiple species, the species of interest were first manually identified in the spatial image. The identification procedure is performed once for the same sample. The image area with the identified species was transformed to a phasor plot. Then, by following the same procedure of simple fitting and error analysis calculation, an uncertainty area was determined. It is noted that one species of interest was processed at a time. Therefore with N species, N uncertainty areas will be defined. The above procedures were coded and performed with Matlab.

Phasor Error Analysis of Single Fluorophores:

Before phasor error analysis, FLIM images were binned to obtain the average peak intensity of 150-200 photons for an image for sufficient signals to analyze. Phasor error analysis was applied to FLIM images acquired from free nicotinamide adenine dinucleotide (NADH) and free flavin adenine dinucleotide (FAD) solutions. The points or the lifetime distributions on the phasor plots were quantitatively analyzed with error analysis. Free NADH has a smaller lifetime distribution, tilt to the right. Free FAD has a larger lifetime distribution, tilt to the left. Circles, indicating the 1-σ uncertainty areas, successfully characterized the size and the shape of the lifetime distributions.

Phasor Error Analysis to Distinguish Tissue Constituents in FLIM Images:

3 channels of optical intensity images and 1 FLIM image are acquired from a tissue-engineered construct. The construct had tissue constituents including cells and extracellular matrix keratin and collagen. The channel 1 optical intensity image shows all three tissue constituents. The channel 2 image shows mainly keratin and collagen. The second harmonic generation (SHG) channel shows only collagen. Single channel NAD(P)H FLIM image was acquired from the engineered tissues. A fast FLIM map, post processed with the Markov Random field technique to clump related areas, can also be generated. The fast FLIM map show some features of collagen. However, keratin is indistinguishable. None of these images alone can distinguish multiple species in an image.

Phasor plots of the NAD(P)H FLIM image can also be generated and show a distribution of phasor points with their weights. A magnified phasor plot can show individual phasor points. Phasor error analysis can then be applied to the FLIM image. For embodiment, in one embodiment, binning was performed to obtain the average peak intensity of 150-200 photons for an image.

Phasor Error Analysis Distinguished Thermally-Stressed from Control Engineered Tissues:

NAD(P)H FLIM images are acquired from engineered tissues had signals from cells and extracellular matrix, collagen and keratin. When assessing cellular viability, the extracellular matrix usually interfered with the assessments. Thus, phasor error analysis was applied to exclude those unwanted signals.

Phasor Error Analysis Defined the Uncertainty Areas of Collagen and Keratin:

Points lying within a particular region were defined as signals from the extracellular matrix. Points lying within another region were defined as cellular signals.

Five control tissue-engineered constructs manufactured with primary human cells from 5 batches (30 control FLIM images) were analyzed. One average fluorescence decay of the extracellular matrix, collagen and keratin, and one average fluorescence decay of the cells were plotted. The plot shows that cells have shorter lifetimes than the extracellular matrix. Phasor error analysis enables automatic separation of extracellular signals from cellular signals without manually selecting regions of interest for each image before cellular viability assessments.

FLIM was also employed to characterize the cellular viability of five batches (5 batches) of tissue-engineered constructs. For each batch, one control construct and one thermally-stressed construct were manufactured. FLIM images acquired from the 5 control and the 5 thermally-stressed constructs were processed with phasor error analysis. Extracellular matrix signals were excluded from the cellular viability assessment. Since one FLIM image provides numerous points on the phasor plot, the transformed phasor points were averaged to one for each FLIM image. The resulting phasor plot shows 30 averaged control and 18 averaged thermally-stressed Bar plots show that the phasor coordinates, g and s, and the parameter g/s significantly distinguished between the control and the thermally-stressed engineered tissues (**P-value <0.001 for 5 batches with 30 controls and 18 thermally-stressed constructs for all parameters).

Phasor error analysis was developed to visualize tissue constituents in one-channel FLIM images. Quantitative derivation of the algorithm was detailed and verified with biologically relevant fluorophores. Free NADH and FAD solutions were chosen because they are biologically relevant and have a reported lifetime of 0.5 and 3 ns, which respectively lies on the right and the left side in the phasor plot. In addition, the method assessed single channel FLIM images acquired from tissue-engineered constructs. Since the engineered tissues were manufactured with human primary cells, individual tissue growth has high variability, depending on the patient's cell viability. Therefore, images of one group of thermally-stressed constructs have mostly extracellular matrix in an image because cells did not grow. Alternatively, images of another group of thermally-stressed constructs still have cells although with low viability. Interestingly, the first group of tissues assists in the viability assessment because they have high average fluorescence lifetimes due to the extracellular matrix. The extracellular matrix has a fluorescence lifetime longer than cells. Thus, images with more keratin or collagen have longer average fluorescence lifetime. This matches the expectation that thermally-stressed constructs have an average lifetime longer than the control constructs. However, the assessment is not for cells and thus not appropriate for the cellular viability assessment.

The resulting phasor plot can only distinguish between the control and the stressed with one parameter (the s coordinate).

The second group of tissues has cells present. Phasor error analysis excluded unwanted extracellular signals and directly assessed cellular viability. The result successfully assessed the cellular viability with all the three parameters (g and s coordinates, and g/s). In conclusion, phasor error analysis provides a useful tool to quantitatively evaluate the points (lifetime distribution) on the phasor plots and to distinguish different species. Thus, in addition to the phasor plot's advantages of direct, rapid interpretation and visualization of the FLIM images, phasor error analysis can quantitatively determine the pseudocolored map and assess species of interest to provide users a useful tool in objectively assessing the acquired FLIM images.

Label-free optical metrics was performed to assess the viability of tissue-engineered constructs with a range of states of tissue viability, controlled with rapamycin treatments. The assessments were compared to standard procedures, including histology, immunohistology, and the cell viability assay. The optical metrics highly correlated to the standard procedure, demonstrating the method's sensitivity. Rapamycin-treated engineered tissues with a range of states of tissue viability was characterized with optical measures, standard cellular viability assay (WST-1), histology, and immunofluorescence histology. The result shows a high correlation between WST-1 and optical redox metrics. A moderate correlation was found between histology and optical metrics. The spatial selectivity of label-free nonlinear imaging microscopy was demonstrated to monitor multiple locations in engineered tissues, useful for identifying non-viable locations in tissues. Rapamycin treatment during the cell culture stage was identified to improve tissue growth in the poorly-growing batches.

Rapamycin, a specific inhibitor of the mammalian target of rapamycin, maintains primary human oral keratinocytes as an undifferentiated cell population capable of retaining their proliferative capacity. Rapamycin treatment controls cellular proliferation in culture and in engineered tissues, creating a range of states of tissue viability. The viability difference between control and rapamycin-treated engineered tissues was smaller than that induced by thermal- and metabolic-stress, thus challenging and testing the sensitivity of our detection technology. The viability of control, rapamycin-treated, and thermally-stressed tissues was assessed by quantitative histology scoring, WST-1 cell viability assay, and label-free optical metrics. The results were compared and correlated to demonstrate their capabilities in safely and effectively assessing engineered tissues.

Tissue-engineered constructs were manufactured with oral keratinocytes freshly harvested from 10 individual patients. With one patient's cells, one batch of tissue-engineered constructs was cultured. The one batch included control constructs and constructs treated with rapamycin or thermal-stress. Tissue-engineered constructs were assessed by standard assays and optical methods.

A section was sliced across the construct, near the edge, fixed in 10% phosphate buffered formalin, and embedded in paraffin for hematoxylin and eosin (H&E) histology and immunohistochemistry (IHC). All the engineered tissues were sectioned for histological assessment and some for IHC imaging. Some engineered tissues were randomly selected for punch biopsies for WST-1 assay. The remaining intact constructs were non-invasively assessed with label-free optical imaging. For each construct, three sites were randomly selected for optical imaging. A tissue-engineered construct consists of three layers: keratin, living cellular, and dermal equivalent layer. Thus, for each site, one to two optical images were measured at lower and upper depths for the proliferating basal layer and the differentiating cellular layer respectively. Some sites only had one depth imaged because the sites did not grow analyzable upper cellular layers.

EVPOME Culture Protocols:

Discarded keratinized oral mucosa was collected from patients undergoing minor oral surgical procedures at the University of Michigan (UM) hospital. The UM Medical School Institutional Review Board approved use of the mucosa and patients provided informed consent for research use. The study adhered to the Declaration of Helsinki Guidelines.

The standard culture procedure can be split into two stages: (1) the cell culture stage and (2) the tissue culture stage. In the cell culture stage, primary human oral mucosal tissues were harvested from procured discarded keratinized oral mucosa and cultured according to previously described protocols. Briefly, primary human oral keratinocytes were enzymatically dissociated from the tissue samples. Oral keratinocyte cultures were established in a chemically-defined, serum-free culture medium (EpiLife and EDGS, Invitrogen/Life Sciences) containing 0.06 mM calcium.

In the tissue culture stage, EVPOME constructs were manufactured by first seeding oral keratinocyte on 1 $cm^2$ acellular cadaver skin (AlloDerm®, LifeCell Corporation, Branchburg, N.J., USA). Resulting keratinocytes and AlloDerm® were submerged in medium containing 1.2 mM calcium for 4 days and then raised to an air-liquid phase for an additional 7 days to induce cell stratification and differentiation. Constructs were cultured in incubators at 37° C. with 5% $CO_2$ for all culture days.

Rapamycin Treatment, and Thermal Stressing Procedures 10 batches tissue-engineered constructs manufactured with cells from 10 independent patients were studied: 5 batches for the rapamycin experiment and 5 batches for the thermal-stress experiment. For the rapamycin experiment, 2 nM rapamycin was added in the medium at the cell culture stage for five days prior to tissue-stage culture and/or the tissue culture stage. Therefore, a total of four experimental conditions were created in the rapamycin experiment:

1. Control+control: no rapamycin was added to the cultures during the two stages.
2. Control+rapa: no rapamycin was added to the first cell culture stage medium; rapamycin was added to the second tissue culture stage medium.
3. Rapa+control: rapamycin was added to the first cell culture stage medium; no rapamycin was added to the second tissue culture stage medium.
4. Rapa+rapa: rapamycin was added to the medium used in both the culture stages.

For the thermal-stress experiment, thermally-stressed constructs were cultured at 43° C. for 24 hours beginning on day 9 post-seeding and were returned to normal culture conditions starting day 10. Thermal stressing was expected to culture constructs with the worst viability.

WST-1 Cellular Viability Assay Protocols:

10 µl/well cell proliferation reagent WST-1 (Roche) in 100 µl of culture medium without phenol red (Life Technologies) was added to the punch biopsied engineered tissues, which were incubated for 4 hours at 37° C. and 5% $CO_2$. Then, the sample was shook thoroughly for 1 min on a shaker before measurements. The samples were measured at 440 nm for their absorbance against a background control as blank using a microplate reader.

Ki-67 Immunohistochemistry (IHC) Imaging Protocols:

Engineered tissues were sectioned on a microtome and heated for 20 minutes at 65° C. Slides were deparaffinized in Xylene and then rehydrated through graduated alcohols and in tap water. Antigen retrieval was performed in the Biocare Decloaking Chamber before the staining. Immunoperoxidase staining was performed on the DAKO Auto-Stainer at room temperature with primary antibody Ki-67 (dilution 1:200, Abcam), secondary antibody rabbit HRP polymer (Biocare), DAB chromogen, and hematoxylin counterstain (dilution 1:10, Biocare).

Quantitative Histology Scoring:

All H&E histology slides were assessed by a panel of three blinded expert readers. Classification criteria were previously developed and detailed, where a viability score of 1 (least viable), 2, 3, 4, or 5 (most viable) was used. The classification criteria included the basal cell layer health, the construct cellular organization, and the keratin layer structural quality. The readers individually assigned a score to each EVPOME histology slide, while blinded to the construct condition and to the other readers' scores.

Label-Free Optical Redox Ratio Metrics:

NAD(P)H and FAD fluorescence images were used to derive a redox ratio map, calculated as [FAD]/([NAD(P)H]+[FAD]) at each image pixel. Image processing was performed to denoise and to clump the pixels with strong collagen SHG and keratin signals together. The regions with high background were removed from the fluorescence images.

Histological Assessment of Rapamycin-Treated Tissue-Engineered Constructs:

Quantitative histology scoring was performed to assess tissue morphology. Two groups of cultured cells were categorized: well-growing culture and poorly-growing culture. The well-growing and the poorly-growing cultures were defined by their control+control histology scores. A control+control score >3 is defined as well-growing. A control+control score <=3 is defined as poorly growing.

For the well-growing culture, viable tissue morphology was observed from all the four constructs with high histology scores (>3) across the four histology sections. No obvious difference between constructs was observed. In contrast, for the poorly-growing culture, the overall tissue viability appears non-viable except the rapa+control construct. The control+control, control+rapa, and rapa+rapa constructs had a broken structure with thin cellular and keratin layers. Poor morphology was observed and low histology scores were shown (histology score <=3). However, the rapa+control construct shows distinct cellular and keratin layers (histology score=4.7), indicating a viable tissue-engineered construct. Rapamycin treatment during the cell culture stage improved the poorly-growing culture.

IF Histology of Rapamycin-Treated Tissue-Engineered Constructs:

Histology sections assessed tissue morphology. Ki-67 stained IHC histology assessed cellular functionality. Ki-67 is a biomarker for tissue proliferative capacity. The nuclei stained in dark brown in the tissue construct basal layers indicate high Ki-67 expression, thus highly proliferating basal cells. The well-growing batch, as defined by its control+control histology score, had numerous positive dark brown stained nuclei in all of the four histology sections. Alternatively, the poorly-growing batch had the most Ki-67 expressions in the rapa+control construct while the other constructs had few dark brown nuclei, consistent with the histology result.

Spatial Selectivity of Label-Free Optical Molecular Imaging:

Histology sections assessed tissue morphology and IF histology characterized tissue functionality. Although histology provides spatial information, the method is destructive. The number of histological assessments is limited to the number of sites sectioned due to its invasiveness, thus not suitable for engineered tissues manufactured for human implantation. In contrast, label-free optical molecular imaging non-invasively assessed engineered tissues in real time. The technique can be performed for multiple times at multiple sites, demonstrating its spatial selectivity.

Non-invasively, label-free optical molecular images demonstrate the highly variable tissue growth at different spatial sites. For embodiment, a thin layer of cells can be atop the dermal equivalent layer. This would suggest that the engineered tissue did not grow uniformly. Alternatively, the rapa+control construct in this batch demonstrates a viable tissue construct. Both the histology section and the optical images exhibit full, uniform, and thick cellular and keratin layers, suggesting high tissue viability.

Optical Redox Ratio Metrics Correlated to WST-1 Assay:

Cross-sectioned label-free optical molecular images monitored tissue morphology, similar to histological assessments except that the method is non-invasive. En-face label-free optical molecular images with redox ratio metrics analyzed a construct's functionality by assessing its cellular metabolism. Optical images can be overlaid with two channels: cyan fluorescence mainly from NAD(P)H and collagen, and SHG signals solely from collagen. The collagen signals were removed from the fluorescence images to calculate a redox ratio map. The redox ratio maps demonstrate that the rapa+control construct had a lower redox ratio (greenish) than the control+control construct.

For quantitative comparison of tissue functionality, a WST-1 cellular viability assay was performed. The WST-1 assay monitored intracellular mitochondrial activity, assessed by WST-1 readings of the biopsied tissues. High WST-1 readings indicate high mitochondrial activity. WST-1 assay readings were compared to optical redox ratio metrics. The resulting plot shows a range of states of viability from the designed experiments. The range of viability states characterized by WST-1 assay and optical metrics shows a significant correlation. High WST-1 readings correspond to low redox ratio metrics and vice versa (P-value <0.001 for 5 batches with 16 constructs and 88 optical measurements).

The correlation plot was color coded with experimental conditions. There are six categories: two control+control conditions separated by their histology scores (score >3 is the well-growing control+control and score <=3 is the poorly-growing control+control), three rapamycin treatment experimental conditions, and one thermal stress experimental condition. The poorly-growing control+control constructs had low WST-1 readings. All the control+control constructs had comparable redox ratios, which are lower than the thermally-stressed constructs. The thermally-stressed constructs had the highest redox ratios and low WST-1 readings, indicating low tissue viability. Rapamycin treatment improved the tissue viability with high WST-1 readings and low redox ratios.

WST-1 Assay Correlated to Histological Assessment:

Quantitative histology scoring was compared to WST-1 assay in assessing tissue-engineered constructs with a range of tissue viability. The viability range was detected by the two metrics. A positive correlation between histology scores and WST-1 readings was found, independent of experimental conditions (5 batches with 16 constructs, P-value <0.001). High WST-1 readings correspond to high histology scores, suggesting viable engineered tissues. The WST-1 assay does not have local spatial information. However, it provides objective readings as opposed to the quantitative histological scoring that requires a panel of experts. WST-1 assay and histology destroyed the pieces of tissues analyzed, which cannot be used for implantation.

Optical Metrics Correlated to Histological Assessments

Histology scores were also compared to optical redox ratio metrics. The plot shows the two metrics correlated (P-value=0.007 for 10 batches with 30 tissue-engineered constructs/histology slides and 166 optical measurements). The correlation is especially well in the high range of histology scores (low range of redox ratios). These results show that tissue viability assessed by the three methods, histology, WST-1 assay, and optics, correlated. The three methods reliably assessed engineered tissues with a range of states of viability.

Rapamycin Treatment During the Cell Culture Stage Enhanced Engineered Tissue Viability:

Rapamycin treatment may enhance tissue growth, observed by histology, immunohistology, optics, and WST-1 assay. Rapamycin-treated tissue-engineered constructs (rapa+control, control+rapa, and rapa+rapa) were compared to the control+control constructs. Five batches of tissue-engineered constructs were studied in the rapamycin experiment. Two well-growing batches were excluded from the following comparison because all the constructs showed well-growing tissues in the two batches.

In the three poorly-growing batches, rapamycin treatment during the cell culture stage (rapa+control) was found to significantly enhance the construct growth. As compared to control+control constructs, rapa+control constructs show high WST-1 readings (*P-value <0.001 for 2 batches with 4 measurements from the control+control and 3 measurements from the rapa+control constructs), low redox ratios (*P-value <0.001 for 3 batches with 23 measurements from the control+control and 24 measurements from the rapa+control constructs), and high histology scores (P-value=0.002 for 3 batches with 5 measurements from the control+control and 4 measurements from the rapa+control constructs). The results indicate that rapa+control constructs had high mitochondrial activity, cellular metabolism, and high tissue growth, respectively measured by WST-1 assay, optical metrics, and histology scores. All the three metrics demonstrate that the rapa+control constructs had better tissue viability than the control+control constructs in the poorly-growing batches.

Here, a range of states of tissue viability was created with rapamycin treatments to test the sensitivity of the optical technique. The viability difference between engineered tissues with rapamycin treatments became smaller than the extreme cases, thus more challenging to detect.

Tissue-engineered constructs were assessed by histology scoring, optics, and WST-1 assay. In addition to histological assessments that monitor tissue morphology, WST-1 assay was employed to monitor cellular functionality. Higher correlation between WST-1 readings and optical redox ratio metrics are found than between histology and optical metrics. This would be because both WST-1 assay and optical methods monitor cellular functionality. All the three metrics correlated with each other, indicating that they reliably assessed engineered tissue viability with a range of states of viability, not just for the extreme cases.

Although the three metrics are reliable, WST-1 and histology are destructive. In contrast, label-free optical molecular imaging is non-invasive, which can be performed for multiple times at multiple sites in tissues. The method is beneficial for engineered tissues manufactured in a large scale (10 cm×10 cm). When manufacturing such engineered tissues, non-uniformity is expected. A reliable tool to non-invasively monitor viability at different locations in a large-scale tissue-engineered construct can assist surgeons to find the best locations in the construct.

It was found that rapamycin treatment during the cell culture stage improved the viability of tissue-engineered constructs in poorly-growing culture. This could be because that rapamycin preserved cellular proliferative capability during the cell culture stage. Therefore, during the tissue culture stage when no rapamycin present in the culture medium, the cells with high proliferation capability actively grew. The enhanced tissue viability in the rapa+control constructs as compared to control+control constructs was found from the poorly-growing batches. The well-growing batches had comparable tissue growth among the experimental conditions (control+control, rapa+control, control+rapa, and rapa+rapa).

As described above, sensitivity of label-free optical metrics with the successful assessments of tissue-engineered constructs with a range of states of viability is demonstrated. Label-free optical molecular imaging noninvasively, quantitatively, and reliably assesses tissue-engineered constructs with spatial information and high sensitivity. Using this approach, reliable adjunctive tools could be developed to provide clinicians with quantitative feedback on engineered construct viability, enabling clinicians to select the healthiest engineered constructs for implantation.

Second Set of Examples

This second set of Examples is independent from the first set of examples set forth above.

Ex vivo produced oral mucosa equivalents, i.e., EVPOMEs, are tissue engineered constructs developed as a viable human graft during a variety of oral surgeries, including procedures that remove oral cancers. EVPOMEs are cultured in batches from a singular human donor. The optical techniques and analysis methods described below describe various release criterion metrics that may be used to assess EVPOME cellular viability prior to surgical use.

Cellular viability quantification from EVPOMEs is especially challenging to obtain because fully developed EVPOMEs typically have three layers: a top keratin layer, a middle living cell layer, and a bottom dermal equivalent layer. The metabolic activity of an EVPOME is typically contained solely within the middle living cell layer. However, the keratin and dermal equivalent layers create signal artifacts due to background fluorescence, scattering, and absorption. Background artifacts are significantly mitigated via two-photon excitation fluorescence microscopy with thin optical sectioning and image processing algorithms. Moreover, the high sensitivity and deep penetration of two-photon fluorescence microscopy enables nonlinear optical assessment of living cells in unstained three-dimensional EVPOMEs with relatively low intracellular fluorescence.

In particular, one or more examples focus on eight potential release criterion metrics including, but not limited to, (1) NAD(P)H Intensity Alone, (2) FAD Intensity Alone, (3) Redox ratio, (4) En-Face Spatial Analysis, (5) Cross-Sectional Cellular Layer Thickness, (6) Bound NAD(P)H Contribution To Fluorescence Lifetime, (7) Average Fluorescence Lifetime, and/or (8) Free FAD Contribution To Fluorescence Lifetime.

All data described below are acquired with a Leica TCS SP5 microscope equipped with a Ti:sapphire laser (Mai Tai, Spectral-Physics). For all measurements: (1) NAD(P)H is excited at 705 nm and detected in the range of 410-500 nm, (2) FAD is excited at 900 nm and detected in the range of 500-590 nm, and (3) second harmonic generation from collagen is excited at 900 nm and detected in the range of 440-460 nm. For cellular monolayer measurements, a 40/63× oil immersion objective is employed with 20 mW of power. For EVPOME measurements, a 25× water immersion objective is employed with 30 mW of power. For FLIM measurements, the laser repetition rate is 100 fs with 4 ps temporal resolution.

More specifically, EVPOMEs within each batch are subdivided into two populations: (1) control EVPOMEs and (2) stressed EVPOMEs. Control EVPOMEs are cultured according to a previously developed 11-day protocol, as described in one or more of K. Izumi, G. Takacs, H. Terashi and S. E. Feinberg, "Ex vivo development of a composite human oral mucosal equivalent," J Oral Maxillofac Surg 57(5), 571-577; discussion 577-578 (1999); K. Izumi, H. Terashi, C. L. Marcelo and S. E. Feinberg, "Development and characterization of a tissue-engineered human oral mucosa equivalent produced in a serum-free culture system," J Dent Res 79(3), 798-805 (2000); K. Izumi, J. Song and S. E. Feinberg, "Development of a tissue-engineered human oral mucosa: from the bench to the bed side," Cells Tissues Organs 176 (1-3), 134-152 (2004); K. Izumi, S. E. Feinberg, H. Terashi and C. L. Marcelo, "Evaluation of transplanted tissue-engineered oral mucosa equivalents in severe combined immunodeficient mice," Tissue Eng 9(1), 163-174 (2003); and/or K. Izumi, S. E. Feinberg, A. Iida and M. Yoshizawa, "Intraoral grafting of an ex vivo produced oral mucosa equivalent: a preliminary report," Int J Oral Maxillofac Surg 32(2), 188-197 (2003), each of which is expressly incorporated herein by reference in its entirety in one or more non-limiting embodiments. Stressed EVPOMEs are those EVPOMEs subjected to alternative culture conditions to create less viable EVPOMEs. In these Examples, four stressing conditions are assessed: (1) thermal stressing, (2) calcium stressing, (3) starvation stressing, and (4) Rapamycin treatment.

(1) For thermal stress, EVPOMEs are incubated at high temperature (43° C.-6° C. elevated relative to control) for 24 hours from day 9 to day 10, thereafter returned to normal conditions.

(2) For calcium stressing, standard culture medium (1.2 mM $Ca^{2+}$) is replaced with a higher concentration of calcium for the duration of EVPOME cultures (2.4, 3.6, or 4 mM $Ca^{2+}$).

(3) For starvation, culture medium is not replenished after day 4.

(4) For Rapamycin treatment, cells are either Rapamycin pretreated (cultured with media including Rapamycin prior to day 0), Rapamycin cultured (cultured with media including Rapamycin starting from day 0), or both.

For each EVPOME, up to three different sites are selected at random to be optically measured. Measurements are obtained at two layers: (1) basal layer (lower) and (2) layer underneath keratin (upper). Only measurements from the lower layer are obtained for EVPOMEs with relatively low cell stratification. For preliminary results, two simplifications are made: (1) measurements from upper and lower layers are grouped for analysis and (2) only one EVPOME per condition per batch is measured (discarding additional EVPOMEs). All statistical analysis is performed with mixed-effects model to account for hierarchical nature of the data where multiple sites are nested within patients.

Results of Experiments

Relative to (1 and 2), fluorescence intensity images are measured from an NAD(P)H and an FAD channel. These measurements are analyzed based on comparing NAD(P)H intensity alone, FAD intensity alone, or with a redox ratio, defined as [FAD]/([FAD]+[NAD(P)H]). High metabolic activity is evaluated in cells as image regions with higher NAD(P)H intensity than average (and typically lower FAD intensity as well). These cells that required higher energy levels produce more NAD(P)H within the mitochondria in order to generate needed ATP.

1. Ex Vivo Produced Oral Mucosal Equivalent (EVPOME) Viability can be Assessed Via Measurements of Fluorescence Intensity from Endogenous Cellular NAD(P)H.

FIGS. 1A and 1B are representative NAD(P)H fluorescence images of control (1A) and starved EVPOMEs (1B) wherein the scale bar is 25 μm. The results of the aforementioned evaluations are set forth in Table 1 below which sets forth experimental conditions and statistical significance validating NAD(P)H fluorescence intensity as a release criterion for EVPOME manufacturing

| Release Criteria: NAD(P)H Fluorescence Intensity | | | |
|---|---|---|---|
| Stressing Conditions | EVPOME or Cells | Number of EVPOMEs/ Number of Total Meas. | p-value (Control vs. Stressed) |
| Thermal | EVPOME (Control) | 5/30 | |
|  | EVPOME (Stressed) | 5/30 | <0.001 |
| $Ca^{2+}$ | EVPOME (Control) | 2/12 | |
|  | EVPOME (3.6 mM $Ca^{2+}$) | 2/8 | <0.001 |
| Rapamycin | EVPOME (Control) | 2/12 | |
|  | EVPOME (Rapamycin pretreated) | 2/9 | 0.005 |
| Starvation | EVPOME (Control) | 3/18 | |
|  | EVPOME (Starved) | 3/15 | <0.001 |

This data shows the metric of quantifying NAD(P)H fluorescence intensity can distinguish thermally—, 3.6 mM $Ca^{2+}$—, Rapamycin pretreated-stressed, and starved EVPOMEs from control with statistical significance 2. EVPOME Viability can be Assessed Via Measurements of Fluorescence Intensity from Endogenous Cellular FAD.

FIGS. 2A and 2B are representative FAD fluorescence images of control and 3.6 mM stressed EVPOMEs wherein the scale bar is 25 μm. The results of the aforementioned evaluations are set forth in Table 2 below which sets forth experimental conditions and statistical significance validating FAD fluorescence intensity as a release criterion for EVPOME manufacturing

| Release Criteria: FAD Fluorescence Intensity | | | |
|---|---|---|---|
| Stressing Conditions | EVPOME or Cells | Number of EVPOMEs/ Number of Total Meas. | p-value (Control vs. Stressed) |
| $Ca^{2+}$ | Cells (Control) | 3/11 | |
|  | Cells (3.6 mM $Ca^{2+}$) | 3/13 | <0.001 |
|  | EVPOME (Control) | 2/12 | |
|  | EVPOME (2.4 mM $Ca^{2+}$) | 2/11 | <0.001 |
|  | EVPOME (3.6 mM $Ca^{2+}$) | 2/8 | 0.004 |
|  | EVPOME (4 mM $Ca^{2+}$) | 2/9 | 0.009 |

-continued

Release Criteria: FAD Fluorescence Intensity

| Stressing Conditions | EVPOME or Cells | Number of EVPOMEs/ Number of Total Meas. | p-value (Control vs. Stressed) |
|---|---|---|---|
| Rapamycin | EVPOME (Control) | 2/12 | |
| | EVPOME (Rapamycin pretreated and cultured) | 2/8 | 0.026 |

This data shows the metric of quantifying FAD fluorescence intensity can distinguish 3.6 mM $Ca^{2+}$-stressed cells from control cells; in addition, 2.4 mM, 3.6 mM, and 4 mM $Ca^{2+}$-stressed, and Rapamycin pretreated and cultured-stressed EVPOMEs from control EVPOMEs with statistical significance.

3. EVPOME Viability can be Assessed Via Ratiometric Analysis of Fluorescence Intensity from Endogenous Cellular NAD(P)H and FAD.

Relative to (3), the metabolic function is assessed via NAD(P)H and FAD fluorescence images of keratinocytes in a monolayer. Because the dish is cultured in an environment favoring cell proliferation and measured when cell confluence reaches 90%, most of the cells have high metabolic activity. Typically, all imaged cells exhibit high NAD(P)H fluorescence around the nuclei but low FAD fluorescence, i.e. cells with high metabolism would have low redox ratios (redox ratio=[FAD]/([NAD(P)H]+[FAD])).

Redox ratio maps are also employed for EVPOMEs. Keratin and collagen background signals are excluded from the redox ratio analysis by image processing algorithms. An average redox ratio for each image is calculated. The result shows that the redox ratios distinguish stressed EVPOMEs from control EVPOMEs, having a higher redox ratio value in stressed samples.

Figure 3B:
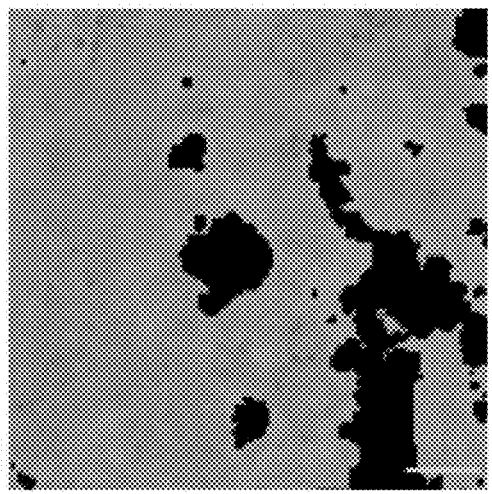

FIGS. 3A and 3B are representative Redox Ratio maps of control and thermally-stressed EVPOMEs wherein the scale bar is 25 μm. The results of the aforementioned evaluations are set forth in Table 3 below which sets forth experimental conditions and statistical significance validating redox ratio as a release criterion for EVPOME manufacturing.

Release Criteria:Redox Ratio

| Stressing Conditions | EVPOME or Cells | Number of EVPOMEs/ Number of Total Meas. | p-value (Control vs. Stressed) |
|---|---|---|---|
| Thermal | Cells (Control) | 4/8 | |
| | Cells (Stressed) | 4/8 | 0.004 |
| | EVPOME (Control) | 5/30 | |
| | EVPOME (Stressed) | 5/30 | <0.001 |
| $Ca^{2+}$ | Cells (Control) | 3/11 | |
| | Cells (3.6 mM $Ca^{2+}$) | 3/13 | <0.001 |
| | Cells (4 mM $Ca^{2+}$) | 3/14 | 0.0048 |
| | EVPOME (Control) | 2/12 | |
| | EVPOME (2.4 mM $Ca^{2+}$) | 2/11 | 0.033 |
| | EVPOME (3.6 mM $Ca^{2+}$) | 2/8 | <0.001 |
| | EVPOME (4 mM $Ca^{2+}$) | 2/9 | <0.001 |
| Starvation | EVPOME (Control) | 3/18 | |
| | EVPOME (Starved) | 3/15 | <0.001 |

This data shows the metric of redox ratio can distinguish thermally—, 3.6 mM, and 4 mM $Ca^{2+}$-stressed cells from control cells; in addition, thermally—, 2.4 mM, 3.6 mM, and 4 mM $Ca^{2+}$-stressed, and starved EVPOMEs from control EVPOMEs with statistical significance 4. EVPOME Viability can be Assessed Via En-Face Spatial Analysis for Tissue Cellular Organization from NAD(P)H Fluorescence Images.

Relative to (4), en-face spatial distribution is quantified with a Fourier technique to characterize the basal layer of EVPOME constructs. A Hurst parameter, relating to the sample's degree of order (i.e. fractal dimension), is extracted from each selected region.

Figure 4A:
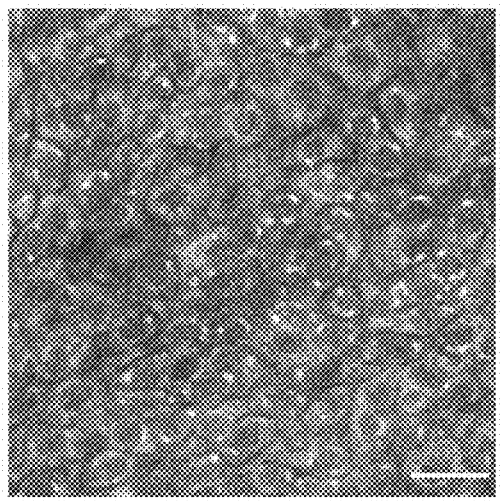
FIGS. 4A and 4B are representative NAD(P)H en-face images of control (4A) and thermally-stressed EVPOMEs (4B) of the Examples wherein the scale bar is 25 μm.
Figure 4B:
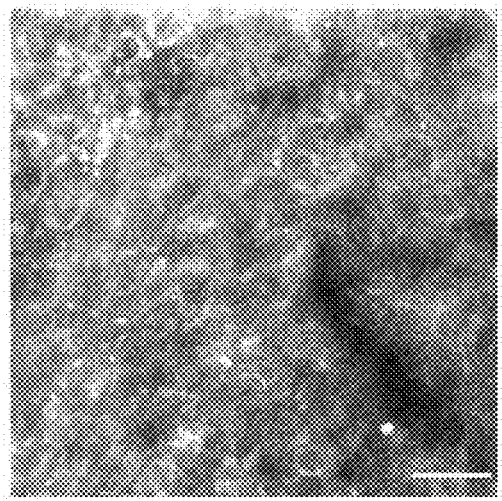

FIGS. 4A and 4B are representative NAD(P)H en-face images of control and thermally-stressed EVPOMEs wherein the scale bar is 25 μm. The results of the aforementioned evaluations are set forth in Table 4 below which sets forth experimental conditions and statistical significance validating en-face spatial analysis for NAD(P)H fluorescence intensity as a release criterion for EVPOME manufacturing Release Criteria: En-face Spatial Analysis

| Stressing Conditions | EVPOME or Cells | Number of EVPOMEs/ Number of Total Meas. | p-value (Control vs. Stressed) |
|---|---|---|---|
| Thermal | EVPOME (Control) | 5/14 | |
| | EVPOME (Stressed) | 5/13 | <0.001 |
| Starvation | EVPOME (Control) | 3/9 | |
| | EVPOME (Starved) | 3/9 | <0.001 |

This data shows the metric of quantifying spatial organization can distinguish thermally-stressed and starved EVPOMEs from control EVPOMEs with statistical significance.

5. EVPOME Viability can be Assessed Via Quantifying Cellular Layer Thickness from Cross-Sectional Optical Images.

Relative to (5), cross-sectional cellular layer thickness is extracted. More specifically, cross-sectional EVPOME images capture the layered structure, cellular layer thickness, and the keratin dissociation from the cellular layer from the stressed EVPOME.

FIGS. 5A and 5B are representative NAD(P)H cross-sectional images of control and Rapamycin cultured EVPOMEs wherein the scale bar is 50 μm. The results of the aforementioned evaluations are set forth in Table 5 below which sets forth experimental conditions and statistical significance validating NAD(P)H cross-sectional imaging as a release criterion for EVPOME manufacturing Release Criteria: Cross-Sectional Imaging

| Stressing Conditions | EVPOME or Cells | Number of EVPOMEs/ Number of Total Meas. | p-value (Control vs. Stressed) |
|---|---|---|---|
| Rapamycin | EVPOME (Control) | 2/3 | |
| | EVPOME (Rapamycin pretreated) | 2/2 | <0.001 |
| | EVPOME (Rapamycin cultured) | 2/3 | <0.001 |
| | EVPOME (Rapamycin pretreated and cultured) | 2/2 | <0.001 |

This data shows the metric of quantifying the thickness of the cellular layer can distinguish Rapamycin pretreated, Rapamycin cultured, and Rapamycin pretreated and cultured-stressed EVPOMEs from control EVPOMEs with statistical significance.

Relative to (6 to 8), fluorescence lifetime images are measured from an NAD(P)H and/or FAD channel. Fluorescence decays are best fit with a two-component exponential model using a least-squares iterative fit (SymPhoTime, Leica). These models enable extraction of time-resolved decay kinetics of NAD(P)H and/or FAD including bound NAD(P)H contribution, average fluorescence lifetime, and/or free FAD contribution. In addition, FLIM images are analyzed with exponential fitting and phasor analysis by extracting time-resolved fluorescence decays either from individual cells (monolayer samples) or regions void of collage fluorescence, as described above. After extracting a time-resolved decay, a mathematical model is employed to characterize the decay with both a bi-exponential decay model (Picoquant GmbH, Germany) and a phasor analysis algorithm. Prior to phasor analysis, each fluorescence decay is shifted prior to transformation so that the fluorescence peak is at time=0.

In addition, extracted fluorescence decays are best-fit to a two-exponential model. All fitting is performed with an iterative least-squares model employing SymPhoTime software (PicoQuant GmbH, Germany). A common IRF is deconvolved with the model, measured as the SHG emission from a collagen sample. Fitting parameters include two lifetime parameters and their corresponding amplitudes, intensity background correction, IRF time shift, and IRF intensity background correction. Free NAD(P)H can exhibit a short lifetime ($\tau 2$) while bound NAD(P)H typically exhibits a long lifetime ($\tau 1$). Alternatively, bound FAD typically exhibits a short lifetime ($\tau 2$) while free FAD typically exhibits a long lifetime ($\tau 1$).

A characteristic difference between stressed and non-stressed cells in the NAD(P)H channel is that there typically is a greater percent contribution from bound NAD(P)H in stressed keratinocytes compared to non-stressed keratinocytes. A characteristic difference between stressed and non-stressed cells in the FAD channel is that there typically is a greater percent contribution from free FAD in non-stressed (control) keratinocytes compared to stressed keratinocytes.

6. EVPOME Viability can be Assessed Via Time Resolved Fluorescence Decay Measurements to Quantify Bound-NAD(P)H Contribution to Fluorescence Lifetime.

FIG. 6 is a line graph illustrating average NAD(P)H fluorescence decays with fits of (C) control and (S) thermally-stressed dish keratinocytes. The results of the aforementioned evaluations are set forth in Table 6 below which sets forth experimental conditions and statistical significance validating quantification of bound-NAD(P)H contribution to fluorescence lifetime as a release criterion for EVPOME manufacturing

| | Release Criteria: FLIM (A1) NAD(P)H | | |
|---|---|---|---|
| Stressing Conditions | EVPOME or Cells | Number of EVPOMEs/ Number of Total Meas. | p-value (Control vs. Stressed) |
| Thermal | Cells (Control) | 3/11 | |
| | Cells (Stressed) | 3/7 | <0.001 |
| | EVPOME (Control) | 2/12 | |
| | EVPOME (Stressed) | 2/10 | <0.001 |
| $Ca^{2+}$ | EVPOME (Control) | 1/3 | |
| | EVPOME (3.6 mM $Ca^{2+}$) | 1/3 | <0.001 |
| Rapamycin | EVPOME (Control) | 2/11 | |
| | EVPOME (Rapamycin pretreated and cultured) | 2/8 | <0.001 |

This data shows that the fluorescence lifetime contribution from bound-NAD(P)H is significantly different between control and stressed samples (thermal, calcium, and Rapamycin stressing) for four experimental comparisons. These results indicate that bound-NAD(P)H may be useful as a release criterion for matured engineered tissues.

7. EVPOME Viability can be Assessed Via Time Resolved Fluorescence Decay Measurements to Quantify Average Fluorescence Lifetime.

Figure 7:
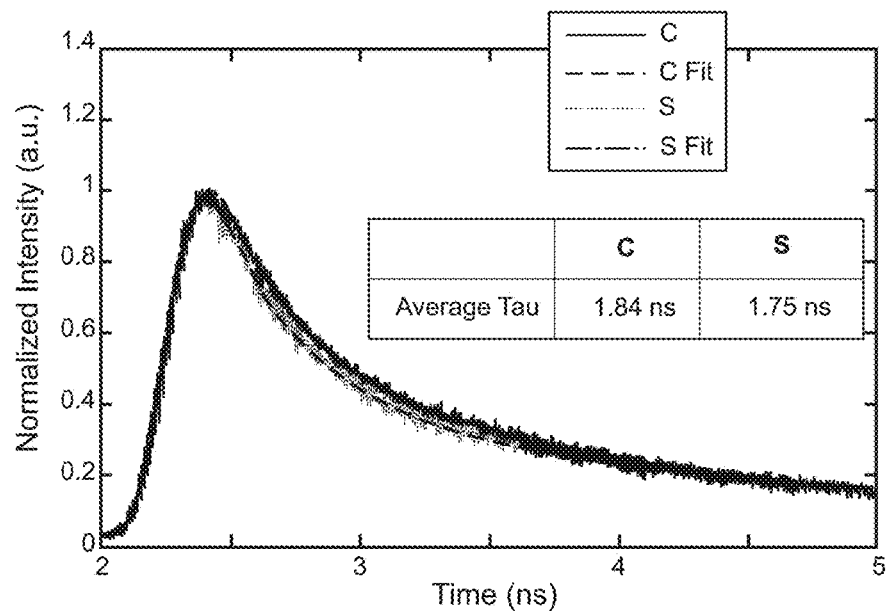
FIG. 7 is a representative line graph illustrating average NAD(P)H fluorescence decays with fits of (C) control and (S) thermally-stressed dish keratinocytes of the Examples.

FIG. 7 is a line graph illustrating average NAD(P)H fluorescence decays with fits of (C) control and (S) thermally-stressed dish keratinocytes. The results of the aforementioned evaluations are set forth in Table 7 below which sets forth experimental conditions and statistical significance validating quantification of NAD(P)H average fluorescence lifetime as a release criterion for EVPOME manufacturing.

| | Release Criteria: FLIM Average Lifetime | | |
|---|---|---|---|
| Stressing Conditions | EVPOME or Cells | Number of EVPOMEs/ Number of Total Meas. | p-value (Control vs. Stressed) |
| Thermal | Cells (Control) | 3/11 | |
| | Cells (Stressed) | 3/7 | 0.03 |
| | EVPOME (Control) | 2/12 | |
| | EVPOME (Stressed) | 2/10 | <0.001 |
| $Ca^{2+}$ | EVPOME (Control) | 1/3 | |
| | EVPOME (3.6 mM $Ca^{2+}$) | 1/3 | <0.001 |
| | EVPOME (4 mM $Ca^{2+}$) | 1/2 | 0.001 |
| Starvation | EVPOME (Control) | 2/12 | |
| | EVPOME (Starved) | 2/10 | <0.001 |

This data shows that the average NAD(P)H fluorescence lifetime is significantly different between control and stressed samples (thermal, calcium, and starvation stressing) for four experimental comparisons. These results indicate that NAD(P)H average fluorescence lifetime may be useful as a release criterion for matured engineered tissues.

8. EVPOME Viability can be Assessed Via Time-Resolved Fluorescence Decay Measurements to Quantify Free FAD Contribution to Fluorescence Lifetime.

Figure 8:
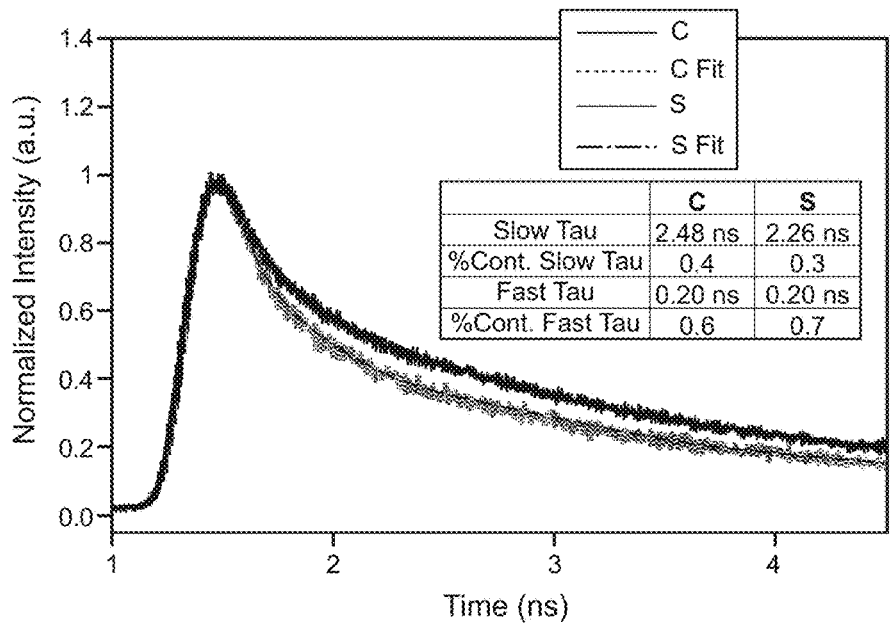
FIG. 8 is a representative line graph illustrating average FAD fluorescence decays with fits of (C) control and (S) thermally-stressed dish keratinocytes of the Examples.
Figure 9:
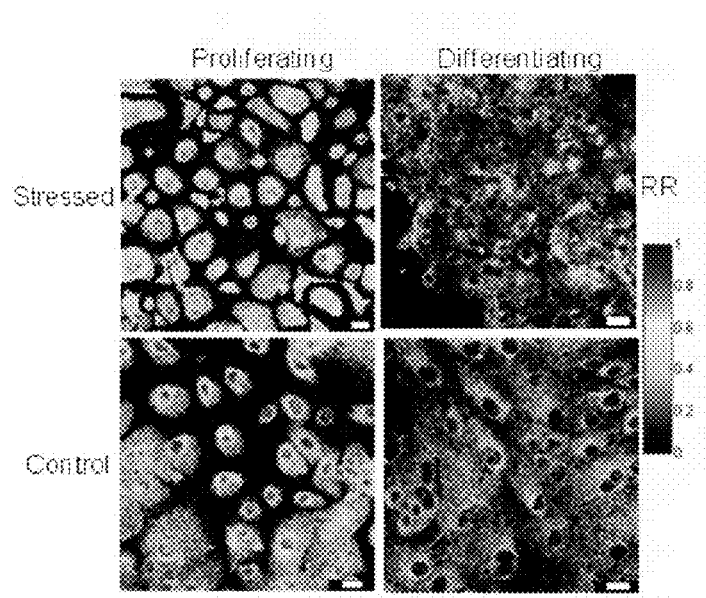
FIG. 9 is an example redox ratio map of control and stressed proliferating and differentiating keratinocytes in vitro wherein shades of grey represent a relative high redox ratios, indicating low metabolic activities, as shown in the top row from the stressed samples while additional shades of grey represent a relative low redox ratio, indicating high metabolic activities, as shown in the bottom row from the control samples, and wherein the scale bar is 25 μm.
Figure 10A:
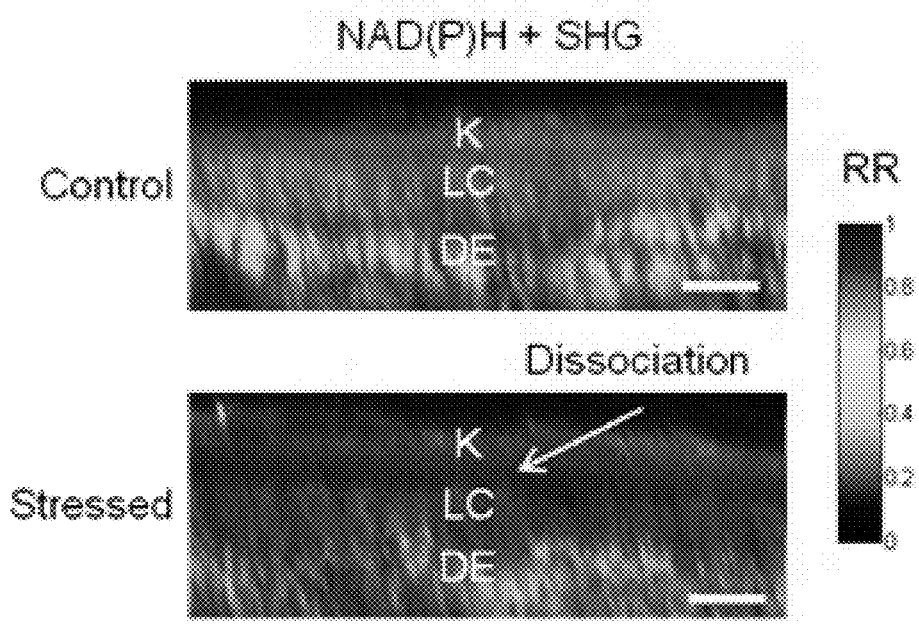
FIG. 10A is an example cross-sectional multiphoton excitation fluorescence image of two EVPOME constructs, each including a top keratin layer (K) about 10-20 μm thick, a middle living cellular layer (LC) about 20-30 μm thick, and a bottom dermal equivalent layer (DE) about 400 μm thick, both control and stressed, from a NAD(P)H channel overlaid with corresponding second harmonic generation (SHG) images, wherein the top row illustrates a viable EVPOME construct while the bottom row illustrates a thermally stressed EVPOME (43° C.)
Figure 10B:
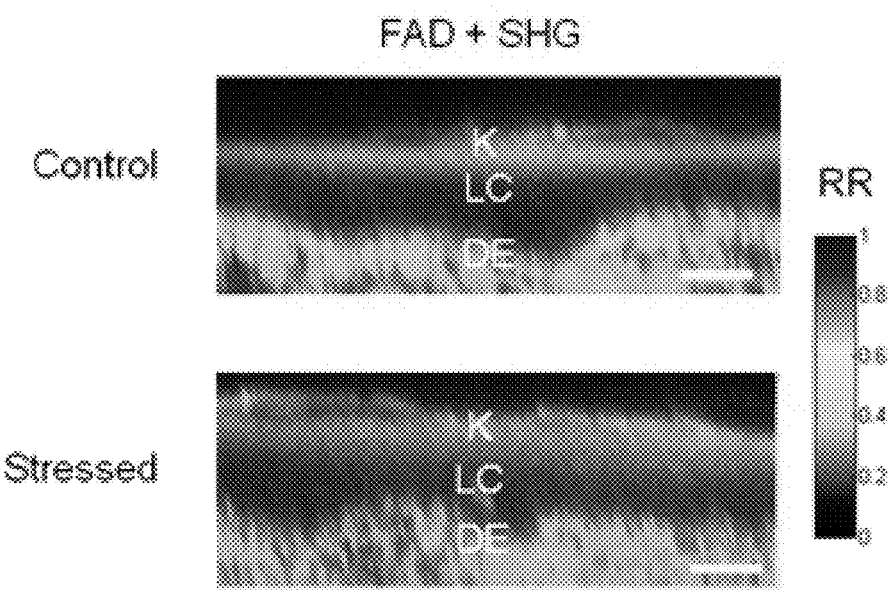
FIG. 10B is an example cross-sectional multiphoton excitation fluorescence image of two EVPOME constructs, each including a top keratin layer (K) about 10-20 μm thick, a middle living cellular layer (LC) about 20-30 μm thick, and a bottom dermal equivalent layer (DE) about 400 μm thick, both control and stressed, from a FAD channel overlaid with corresponding second harmonic generation (SHG) images, wherein the top row illustrates a viable EVPOME construct while the bottom row illustrates a thermally stressed EVPOME (43° C.)
Figure 10C:
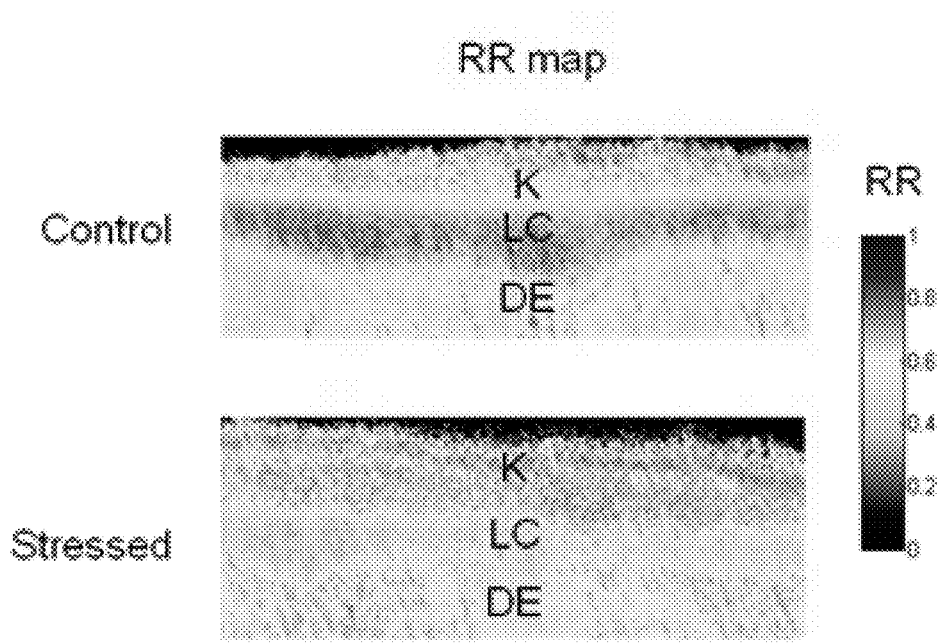
FIG. 10C is an example cross-sectional redox ratio map of two EVPOME constructs, each including a top keratin layer (K) about 10-20 μm thick, a middle living cellular layer (LC) about 20-30 μm thick, and a bottom dermal equivalent layer (DE) about 400 μm thick, both control and stressed, showing that cellular fluorescence from the control constructs has a lower redox ratio than the stressed constructs. the layered structure, wherein the stressed construct shows dissociation of the keratin layer unlike the control construct.
Figure 10D:
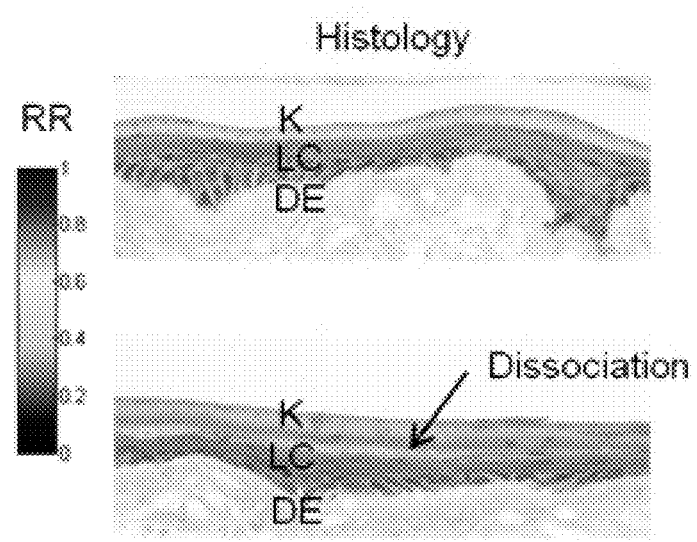
FIG. 10D is an example histological image illustrating cell size and morphology, which is subjective when assessing construct viability, wherein the scale bar is 50 μm.
Figure 11A:
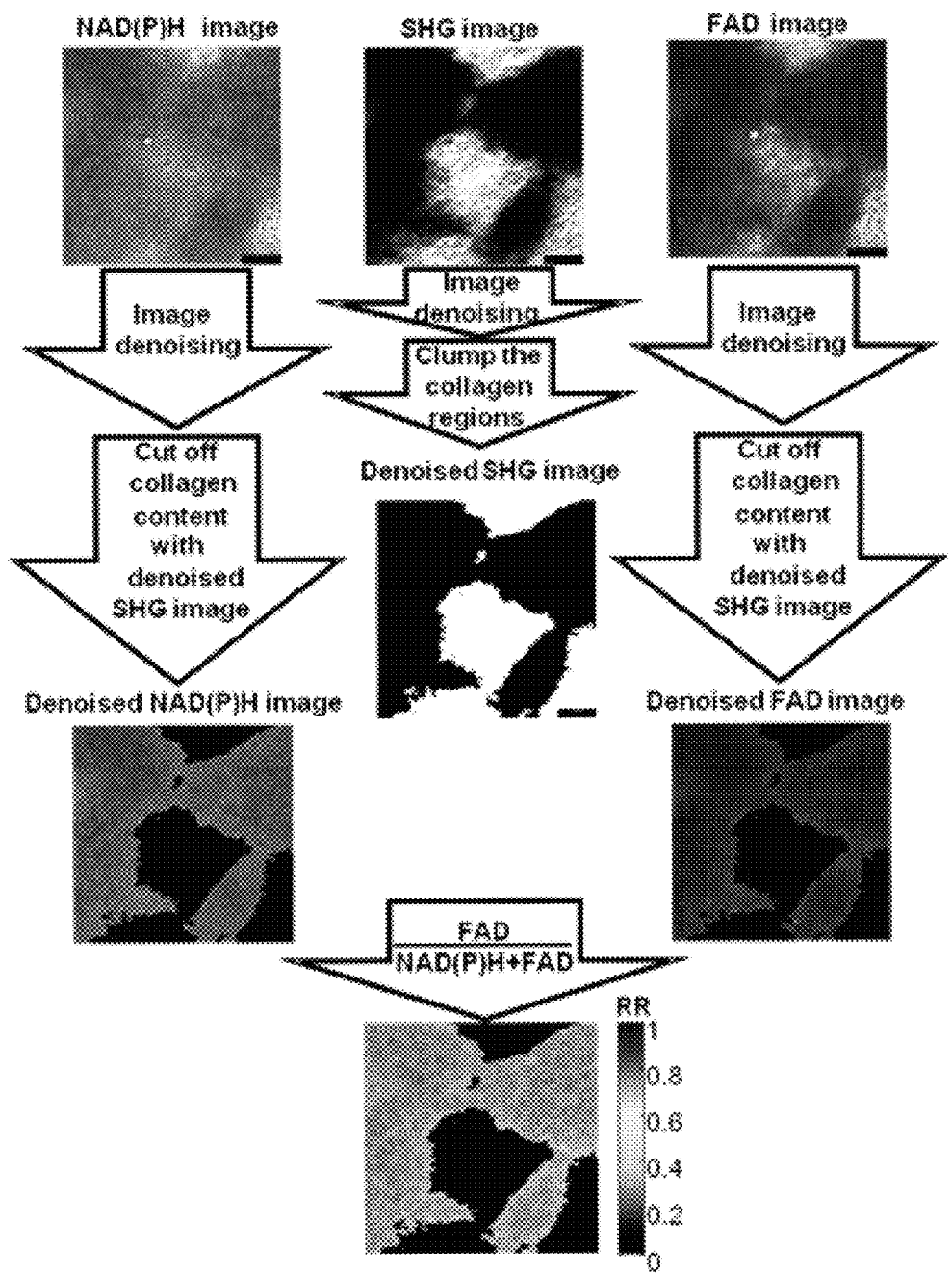
FIG. 11A is an example redox ratio map generation flow chart for a basal cellular layer including collagen.
Figure 11B:
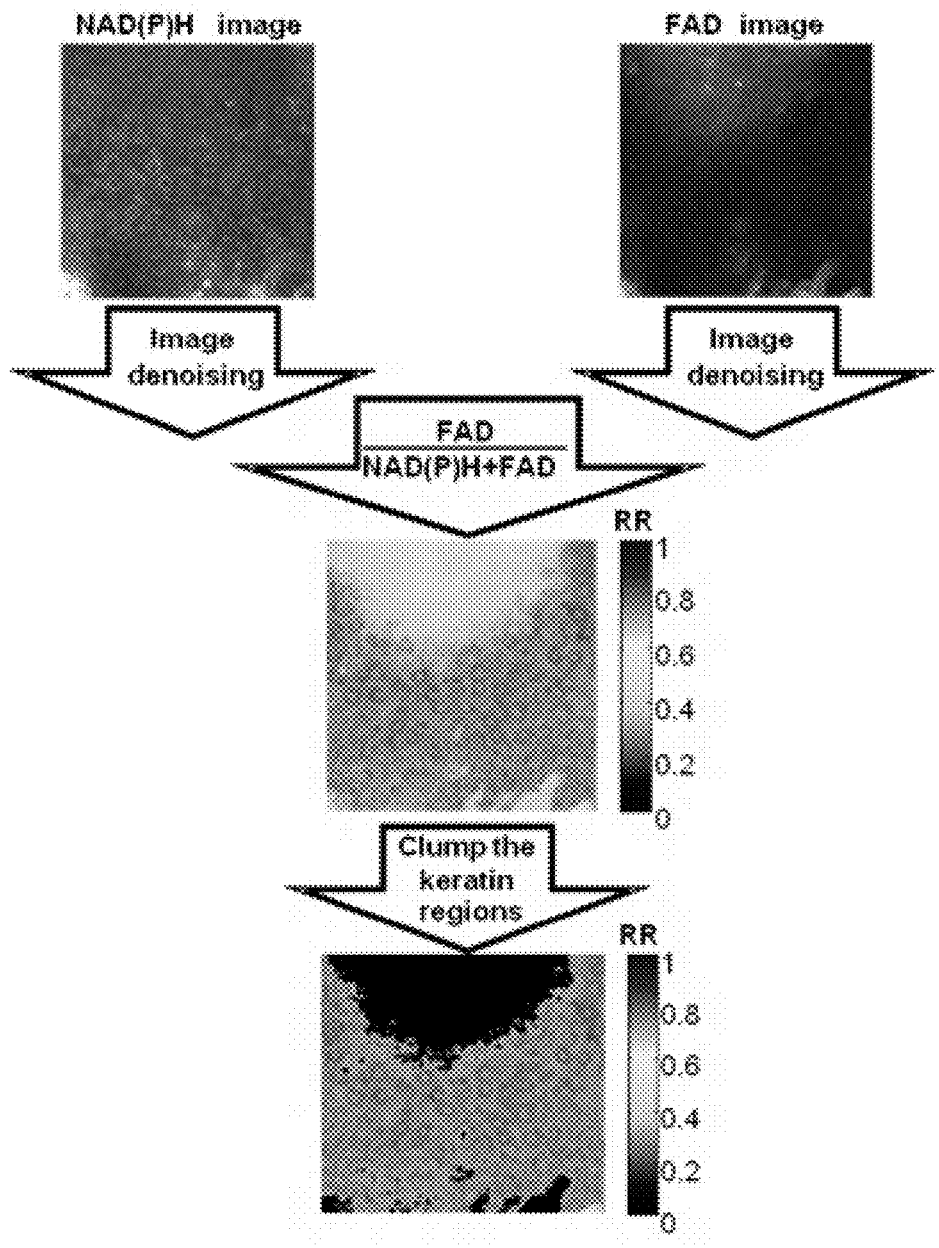
FIG. 11B is an example redox ratio map generation flow chart for an upper cellular layer including keratin.
Figure 12A:
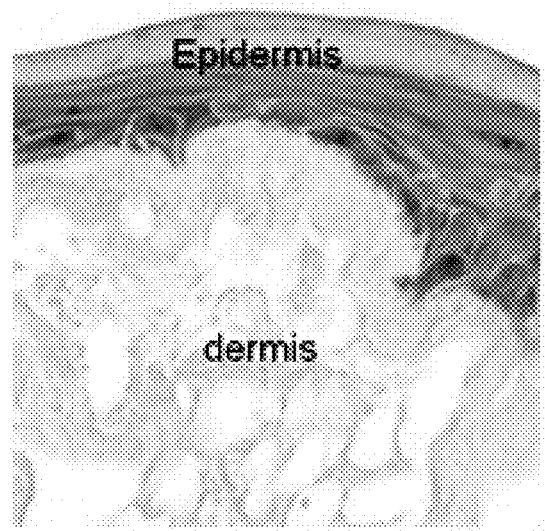
FIG. 12A is an example en-face image of an optically sectioned cellular multiphoton excitation fluorescence image revealing cellular growth and development of an EVPOME construct with endogenous NAD(P)H and FAD.
Figure 12B:
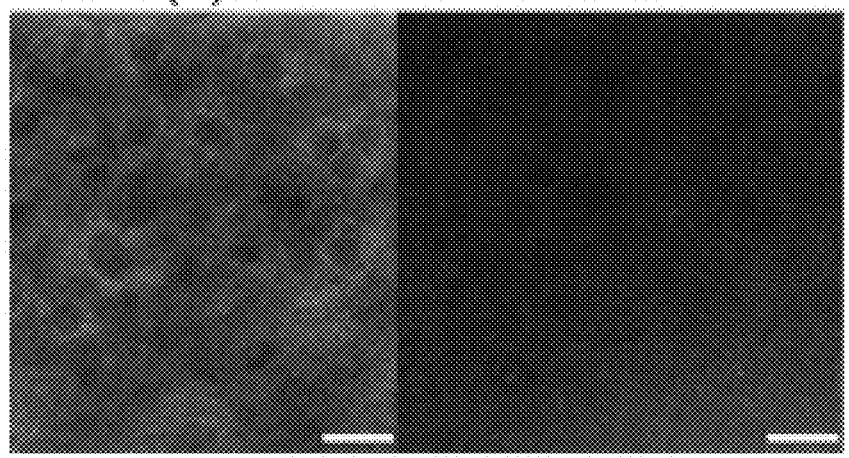
FIG. 12B is an example optically sectioned cellular multiphoton excitation fluorescence image of control upper layer cells including fewer, loosely packed cells, as compared to a basal layer, wherein the scale bar is 25 µm.
Figure 12C:
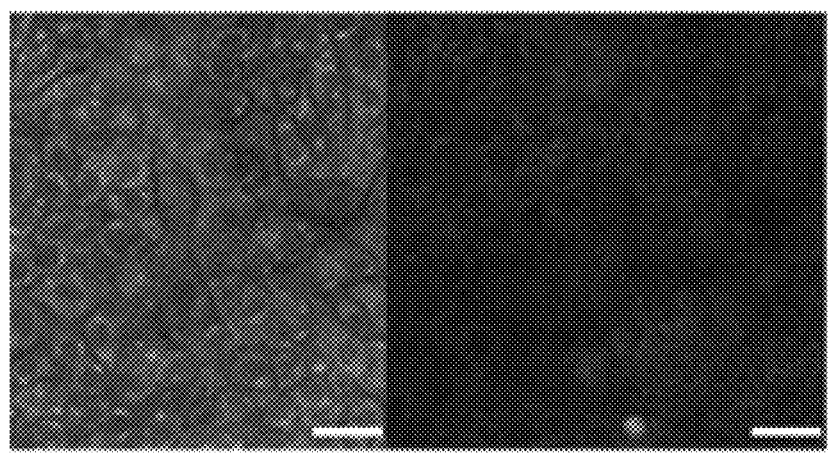
FIG. 12C is an example optically sectioned cellular multiphoton excitation fluorescence image of control basal layer cells including many smaller closely packed cells, wherein the scale bar is 25 µm.
Figure 12D:
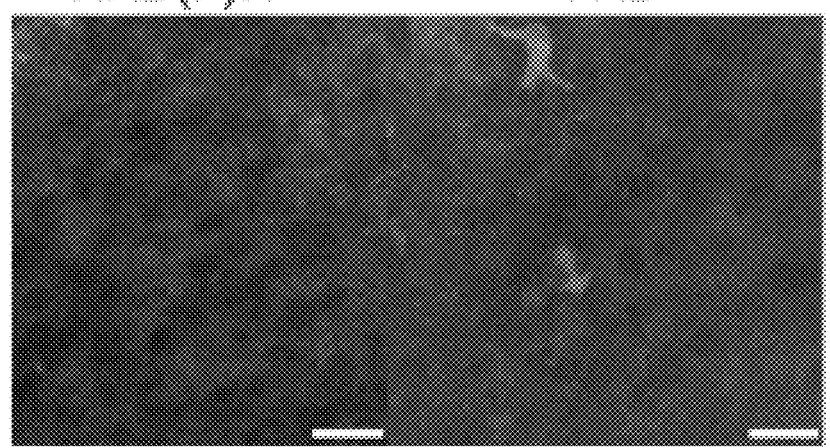
FIG. 12D is an example optically sectioned cellular multiphoton excitation fluorescence image of stressed upper layer cells including fewer, loosely packed cells, as compared to a basal layer, wherein the scale bar is 25 µm.
Figure 12E:
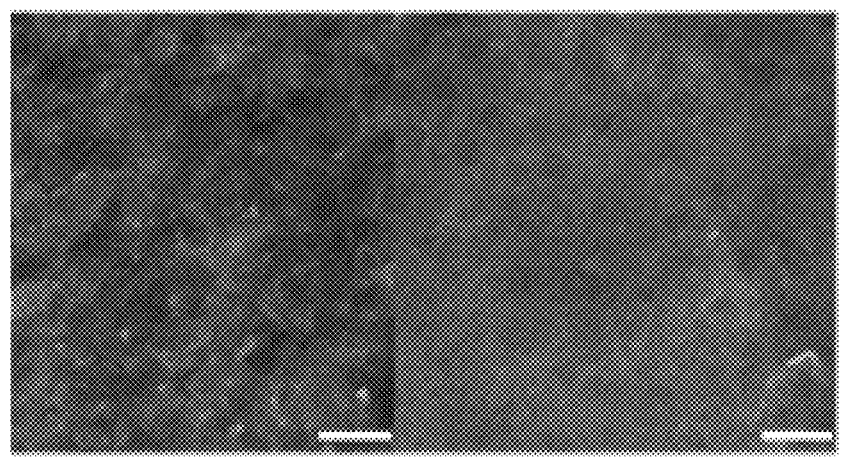
FIG. 12E is an example optically sectioned cellular multiphoton excitation fluorescence image of stressed basal layer cells including many smaller closely packed cells, wherein the scale bar is 25 µm.
Figure 13A:
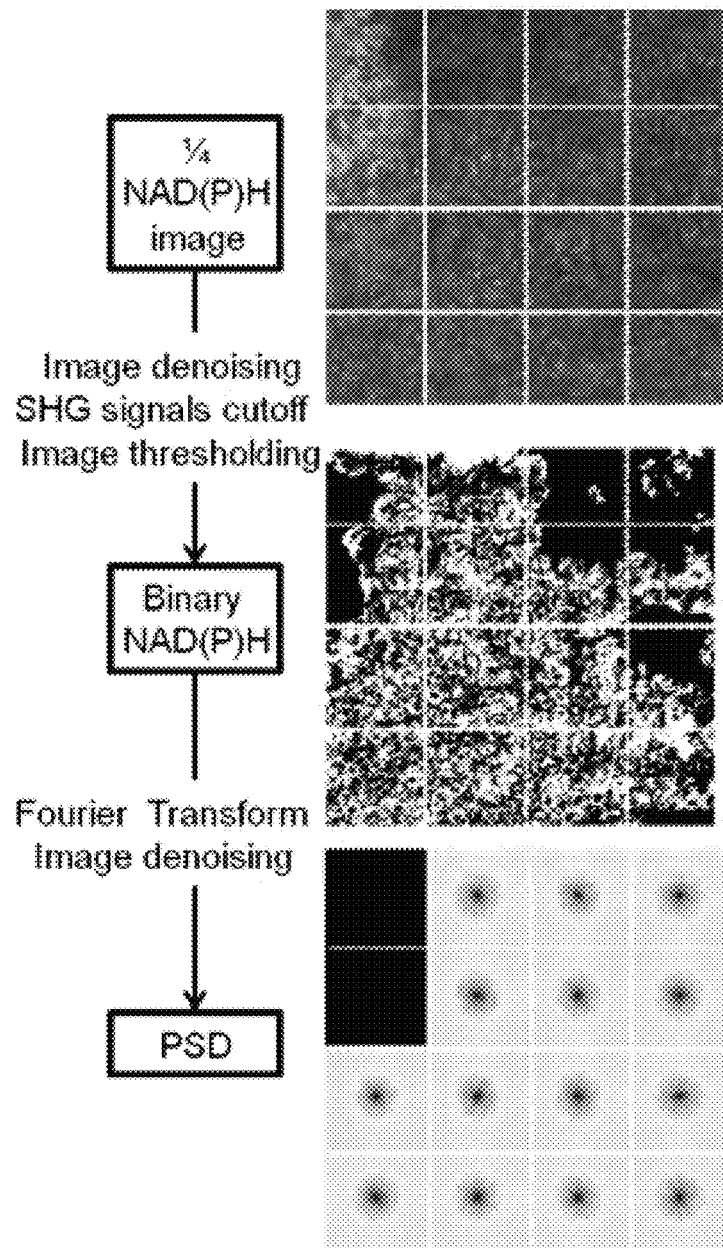
FIG. 13A is an example flow chart of one embodiment of an analysis procedure for a ¼ NAD(P)H image wherein 1/64 sub-images with SHG signals are excluded from the analysis.
Figure 13B:
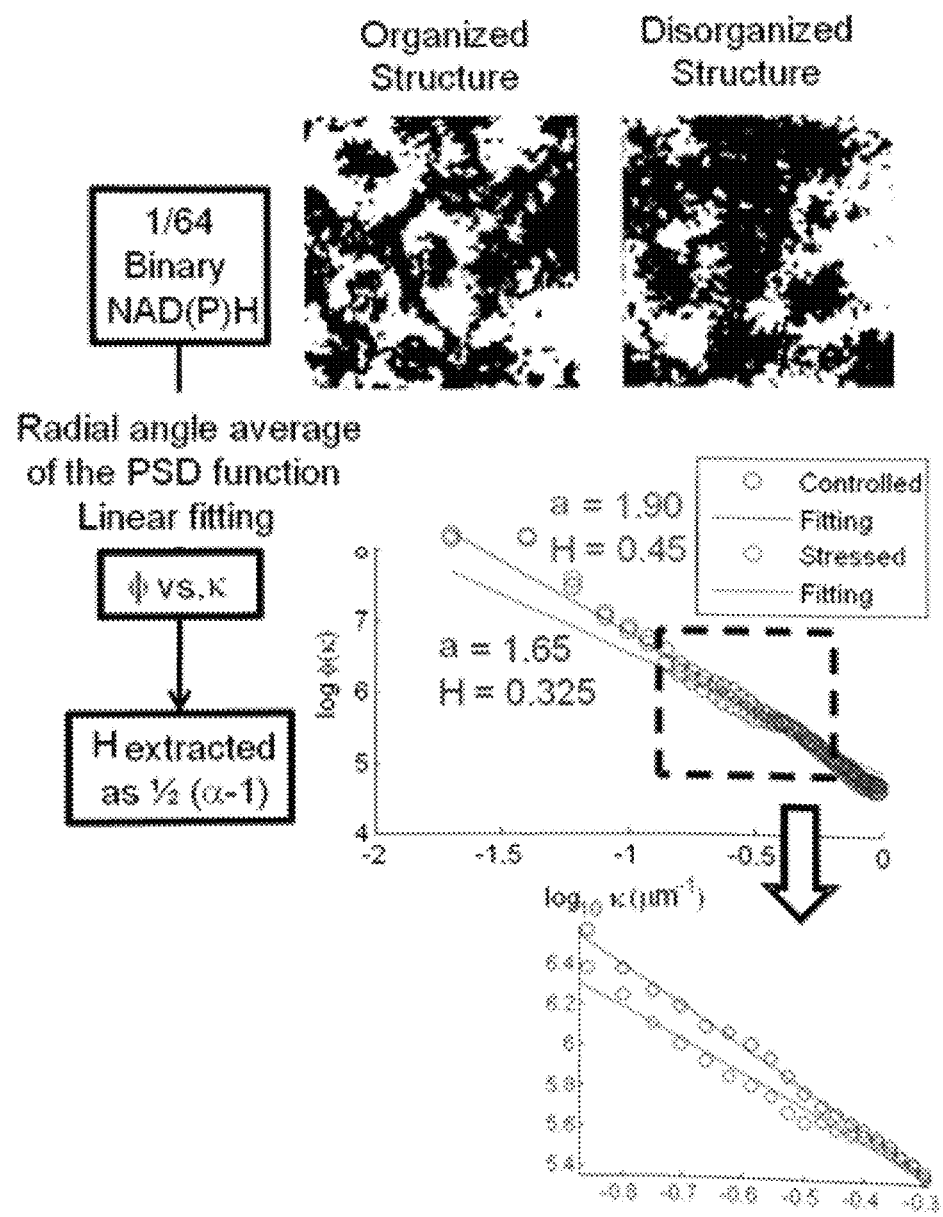
FIG. 13B is a flow chart of another embodiment of an analysis procedure including binary images of organized (left) and the disorganized (right) cell structures wherein the images are post processed with the protocol of the flow charts.
Figure 14A:
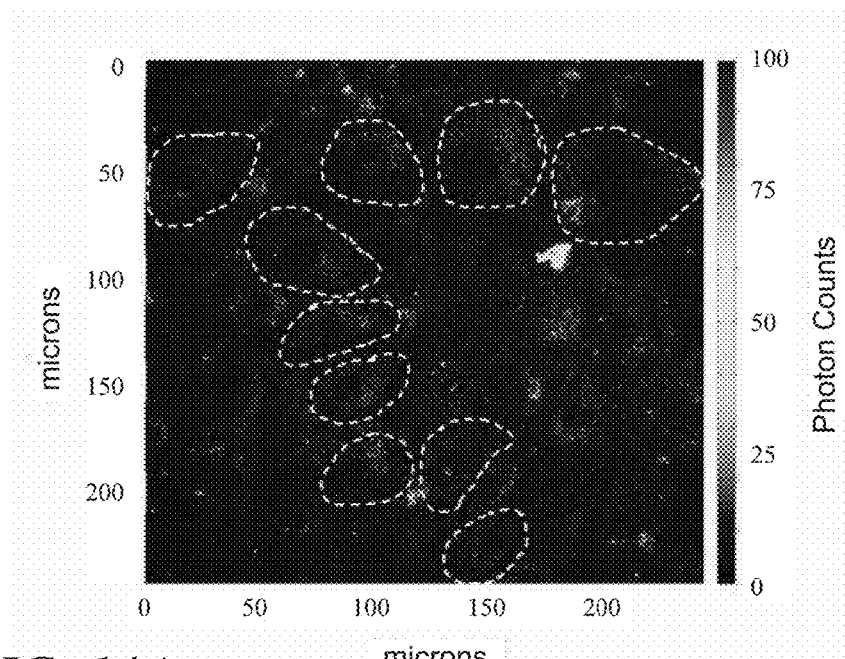
FIG. 14A is an example intensity-modulated FLIM map of (A) control keratinocytes in the NAD(P)H channel.
Figure 14B:
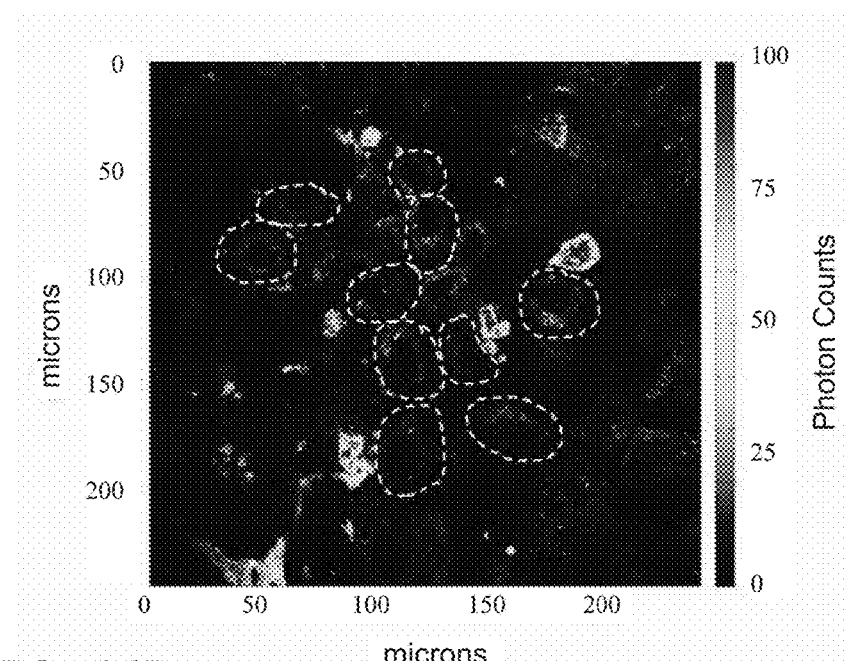
FIG. 14B is an example intensity-modulated FLIM map of (B) stressed keratinocytes in the NAD(P)H channel.
Figure 14C:
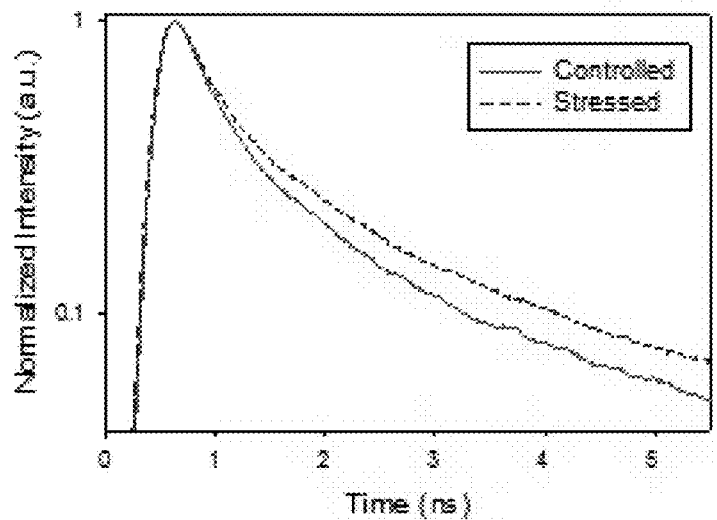
FIG. 14C is an example line graph illustrating ten extracted cellular decays that are obtained from each FLIM measurement, averaged, and smoothed to reduce noise from low photon counts (about 100 counts in peak channel of each measurement)
Figure 15A:
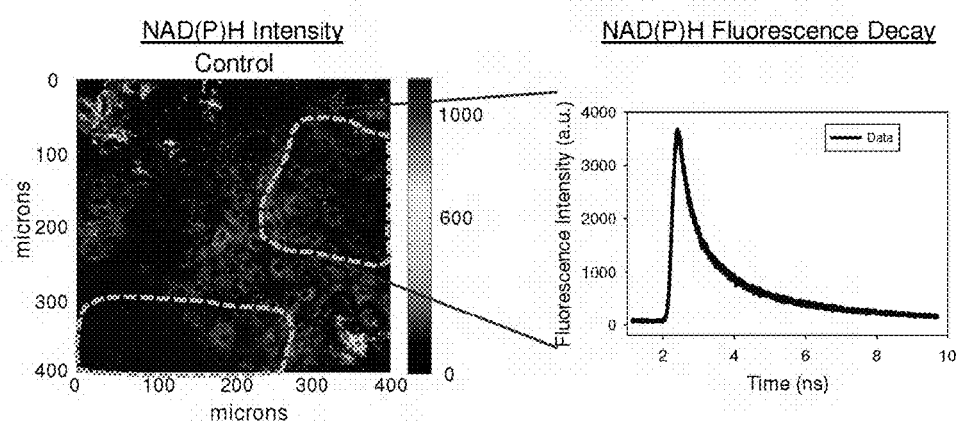
FIG. 15A is an example FLIM image collected from three sites on each EVPOME (top, left) wherein two regions are selected from each image, excluding areas that are high in second harmonic generated signal (top right), wherein all pixels within each region are summed to create a time-resolved decay graph of FIG. 15B.
Figure 15B:
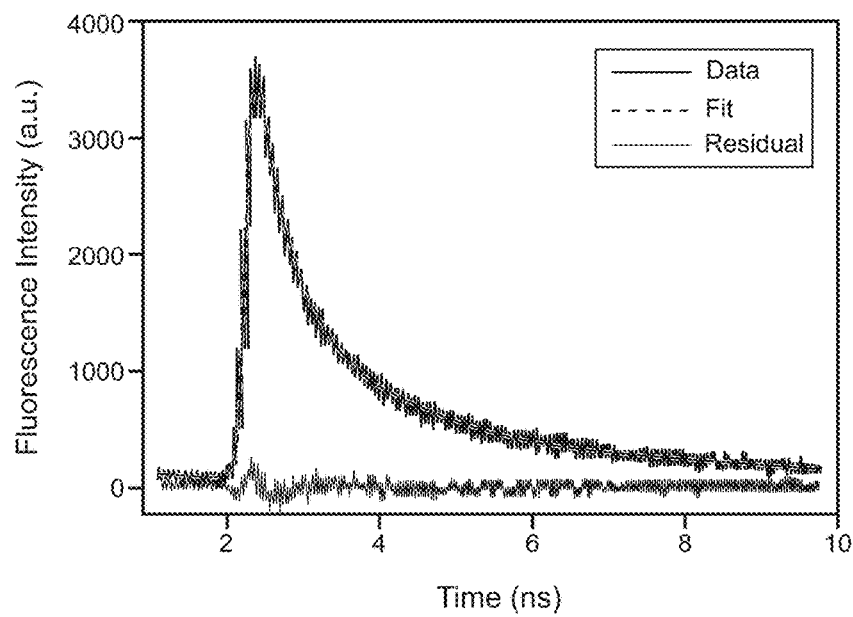
FIG. 15B is an example time-resolved decay line graph wherein fluorescence decay is analyzed using exponential fitting to identify the relative contributions from two species [i.e. bound and free NAD(P)H]
Figure 15C:
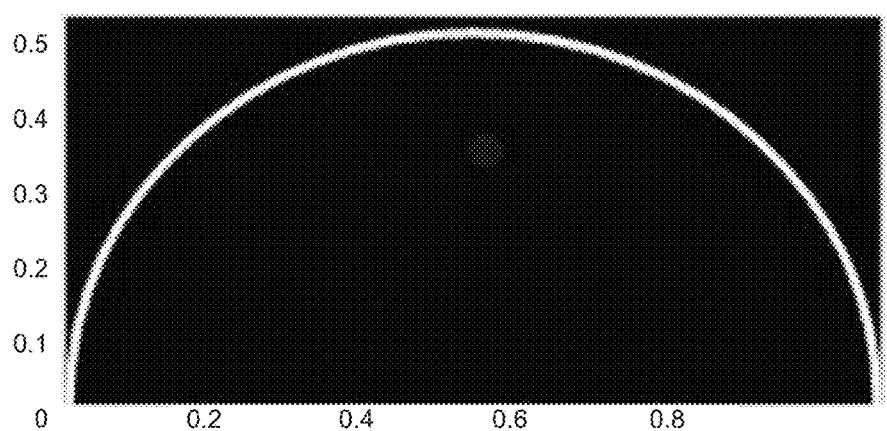
FIG. 15C is an example image generated from analysis of the fluorescence decay of FIG. 15A using phasor analysis.

FIG. 8 is a line graph illustrating average FAD fluorescence decays with fits of (C) control and (S) thermally-stressed dish keratinocytes. The results of the aforementioned evaluations are set forth in Table 8 below which sets forth experimental conditions and statistical significance validating quantification of free FAD contribution to fluorescence lifetime as a release criterion for EVPOME manufacturing.

| Release Criteria: FLIM (A1) FAD | | | |
|---|---|---|---|
| Stressing Conditions | EVPOME or Cells | Number of EVPOMEs/ Number of Total Meas. | Control vs. Stressed) |
| Thermal | Cells (Control) | 2/5 | |
| | Cells (Stressed) | 2/5 | 0.01 |

This data shows that the fluorescence lifetime contribution from bound-FAD is significantly different between control and stressed samples (thermal stressing) for one experimental comparison. These results indicate that bound-FAD may be useful as a release criterion for matured engineered tissues.

The data set forth above and this method demonstrate that early stage development of redox and spatial relationship sensing employed for assessment of tissue-engineered constructs lays the groundwork for creating a quantitative quality control real time method during the entirety of the tissue culturing process. Harvested primary human cell viability can be evaluated at several stages: prior to culture to analyze growth potential, after the first several culture days to determine whether the cells are forming a healthy construct, prior to implantation as a release criterion or to select the best of multiple constructs, and after implantation to test for patient acceptance and transplant viability/function. Nonlinear optical microscopy employed to evaluate local metabolic rates of tissue-engineered constructs provides the foundation for providing quantitative analysis tools during the culture process, allowing for the first time real-time feedback of local cell growth for constructs. The instrumentation and analysis techniques form the foundation for the development of the technology that can be employed for clinical use. Portable equipment with real-time analysis can be developed as an adjunct tool for clinicians to select the most viable tissue-engineered constructs and to assess viability post-implantation. For the first time, this technology will allow clinicians access to quantitative feedback, noninvasively detailing the construct metabolic rate in real time during construct growth prior to implantation. This will assure that the most viable constructs will be implanted, enhancing patient care and treatment.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

What is claimed is:

1. A method of determining the viability of a plurality of living human primary cells obtained from a single human donor for subsequent implantation into the single human donor via quantification of nicotinamide adenine dinucleotide (phosphate) (NAD(P)H), flavin adenine dinucleotide (FAD), and/or collagen, said method comprising the steps of:
   A. providing multi-layered tissue-engineered constructs with each construct including a surface layer, a middle layer containing the plurality of living human primary cells obtained from the single human donor, and a base layer;
   B. contacting the plurality of living human primary cells of each construct with light having a wavelength of from 700 to 900 nm, using two photon excitation, or from 335 to 400 nm, using one photon excitation, to induce an optical response from the NAD(P)H, FAD, and/or collagen;
   C. measuring the optical response;
   D. quantifying one or more of an amount, spatial localization, and/or time-dependent response of the NAD(P)H, FAD, and/or collagen utilizing the optical response to identify viable cells of the plurality of living human primary cells; and
   E. implanting one of the multi-layered tissue-engineered constructs containing the viable cells into the single human donor.

2. The method as set forth in claim 1 wherein the optical response is further defined as fluorescence.

3. The method as set forth in claim 1 wherein the optical response is further defined as second harmonic generation.

4. The method as set forth in claim 1 wherein the step of quantifying is further defined as quantifying an amount of NAD(P)H via measurement of fluorescence.

5. The method as set forth in claim 4 wherein second harmonic generation and FAD measurements are utilized to identify collagen and keratin background regions.

6. The method as set forth in claim 1 wherein the step of quantifying is further defined as quantifying an amount of FAD via measurement of fluorescence.

7. The method as set forth in claim 6 wherein second harmonic generation and FAD measurements are utilized to identify collagen and keratin background regions.

8. The method as set forth in claim 1 wherein the step of quantifying is further defined as ratiometrically analyzing a fluorescence intensity from NAD(P)H and FAD.

9. The method as set forth in claim 8 wherein second harmonic generation and FAD measurements are utilized to identify collagen and keratin background regions.

10. The method as set forth in claim 9 wherein the step of ratiometrically analyzing a fluorescence intensity is performed with a pair of measurements by calculating FAD/(NAD(P)H+FAD) at each pixel after excluding the collagen and keratin background regions.

11. The method as set forth in claim 1 wherein the step of quantifying is further defined as calculating a redox ratio of NAD(P)H and FAD.

12. The method as set forth in claim 1 wherein the step of quantifying is further defined as generating an en-face non-linear optical microscopy spatial image from a NAD(P)H fluorescence image.

13. The method as set forth in claim 12 wherein the step of generating an en-face spatial image is further defined as applying an image processing algorithm.

14. The method as set forth in claim 13 wherein the image processing algorithm is chosen from image denoising/enhancement, background removal, fractal analysis, and combinations thereof.

15. The method as set forth in claim 12 further comprising the step of applying a bi-exponential decay fitting algorithm and/or a phasor analysis algorithm to the en-face non-linear optical microscopy spatial image to determine a fluorescence lifetime image.

16. The method as set forth in claim 1 wherein the step of quantifying is further defined as resolving fluorescence decay measurements to quantify bound-NAD(P)H contributions to fluorescence lifetime.

17. The method as set forth in claim 16 wherein the step of resolving comprises selecting two collagen-free regions of NAD(P)H fluorescence that are void of collagen fluorescence and that have at least 100 photon counts in a peak channel.

18. The method as set forth in claim 17 further comprising the step of applying a least-squares iterative fit with a double exponential model to extract individual and average lifetimes and total contribution of a slow lifetime component.

19. The method as set forth in claim 18 wherein the total contribution is further defined as a contribution from bound-NAD(P)H and has a lifetime of from 1 to 4 nanoseconds.

20. The method as set forth in claim 1 wherein the step of quantifying is further defined as resolving fluorescence decay measurements to quantify average fluorescence lifetimes.

21. The method as set forth in claim 20 wherein the step of resolving comprises selecting two collagen-free regions of NAD(P)H fluorescence that are void of collagen fluorescence and that have at least 100 photon counts in a peak channel.

22. The method as set forth in claim 21 further comprising the step of applying a least-squares iterative fit with a double exponential model to extract individual and average lifetimes and total contribution of a slow lifetime component.

23. The method as set forth in claim 22 wherein the total contribution is further defined as a contribution from bound-NAD(P)H and has a lifetime of from 1 to 4 nanoseconds.

24. A method of determining the viability of a plurality of living human primary cells obtained from a single human donor for subsequent implantation into the single human donor via quantification of nicotinamide adenine dinucleotide (phosphate) (NAD(P)H) and/or flavin adenine dinucleotide (FAD), said method comprising the steps of:
  A. providing multi-layered tissue-engineered constructs with each construct including a surface layer, a middle layer containing the plurality of living human primary cells obtained from a single human donor, and a base layer;
  B. exciting the plurality of living human primary cells of each construct with light having a wavelength of from 700 to 900 nm, using two photon excitation, or from 335 to 400 nm, using one photon excitation, to induce fluorescence from the NAD(P)H and/or FAD;
  C. measuring the fluorescence;
  D. quantifying the presence of NAD(P)H and/or FAD utilizing the fluorescence to identify viable cells of the plurality of living human primary cells; and
  E. implanting one of the multi-layered tissue-engineered constructs containing the viable cells into the single human donor.

* * * * *